(12) United States Patent
Bateman et al.

(10) Patent No.: US 6,992,283 B2
(45) Date of Patent: Jan. 31, 2006

(54) MASS SPECTROMETER

(75) Inventors: Robert Harold Bateman, Knutsford (GB); John Brian Hoyes, Stockport (GB); James Ian Langridge, Sale (GB); Jason Lee Wildgoose, Stockport (GB)

(73) Assignee: Micromass UK Limited, Manchester (GB)

( * ) Notice: Subject to any disclaimer, the term of this patent is extended or adjusted under 35 U.S.C. 154(b) by 117 days.

(21) Appl. No.: 10/739,041

(22) Filed: Dec. 19, 2003

(65) Prior Publication Data

US 2004/0245452 A1    Dec. 9, 2004

Related U.S. Application Data

(60) Provisional application No. 60/477,054, filed on Jun. 10, 2003.

(30) Foreign Application Priority Data

Jun. 6, 2003    (GB) .................................. 0313054

(51) Int. Cl.
*H01J 49/00*    (2006.01)
(52) U.S. Cl. ........................ 250/287; 288/281; 288/282

(58) Field of Classification Search ..................... None
See application file for complete search history.

(56) References Cited

U.S. PATENT DOCUMENTS

| 4,823,368 A |  | 4/1989 | Uda et al. |  |
|---|---|---|---|---|
| 5,073,713 A |  | 12/1991 | Smith et al. |  |
| 6,906,320 B2 | * | 6/2005 | Sachs et al. | ................ 250/282 |

FOREIGN PATENT DOCUMENTS

| DE | 2205713 |  | 8/1973 |
|---|---|---|---|
| EP | 1378930 | A2 | 1/2004 |
| GB | 2382919 | A | 6/2002 |
| GB | 2381948 |  | 5/2003 |
| GB | 2389704 | A | 12/2003 |
| GB | 2392304 | A | 2/2004 |

* cited by examiner

*Primary Examiner*—Nikita Wells
*Assistant Examiner*—Zia R. Hashmi
(74) *Attorney, Agent, or Firm*—Diederiks & Whitelaw, PLC

(57) ABSTRACT

A mass spectrometer is disclosed wherein ions are passed through an ion mobility separator and are then mass analysed by a Time of Flight mass analyzer. Multiple sets of mass spectral data are obtained which are then post-processed so that mass spectral data relating to ions having undesired charge state(s) is filtered out. The resultant mass spectrum comprises ions having a desired charge state.

108 Claims, 19 Drawing Sheets

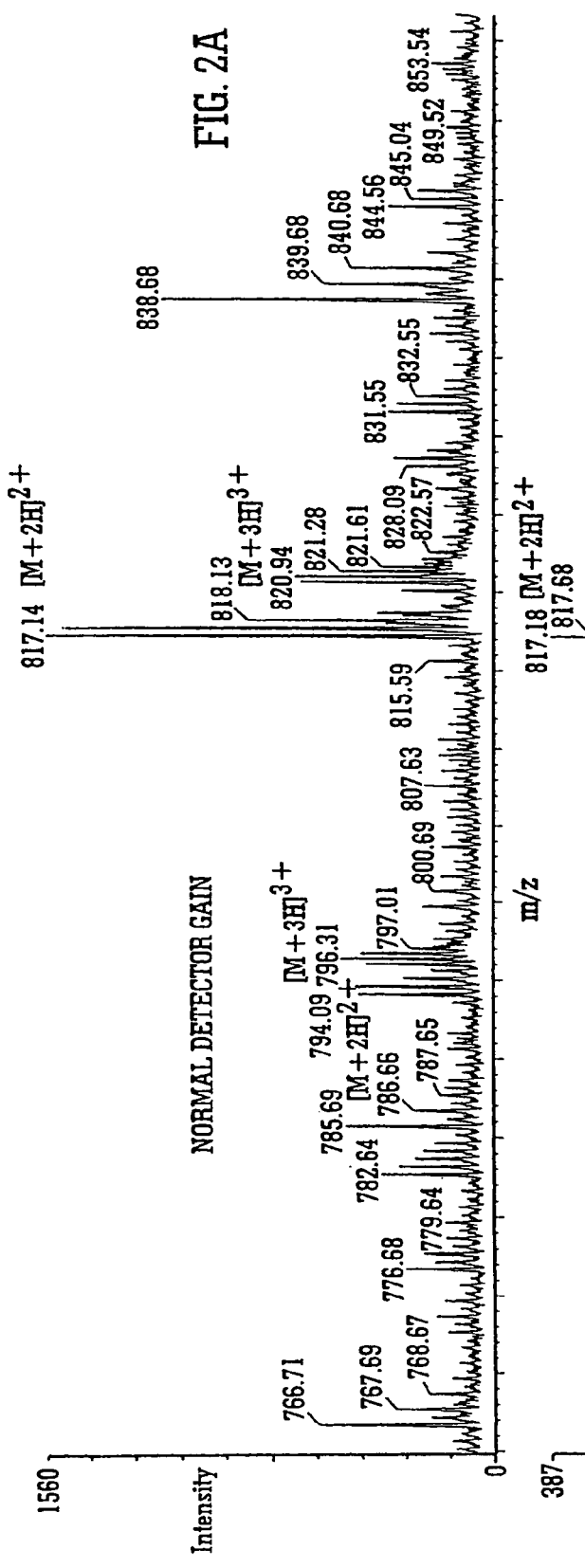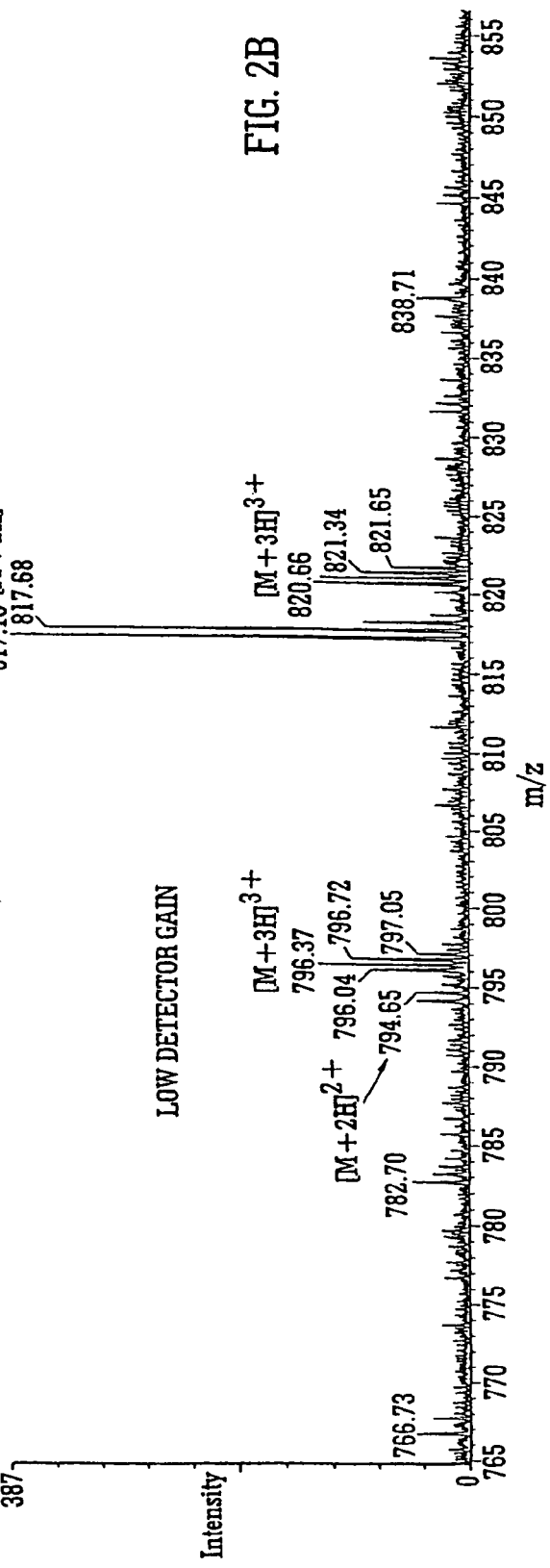

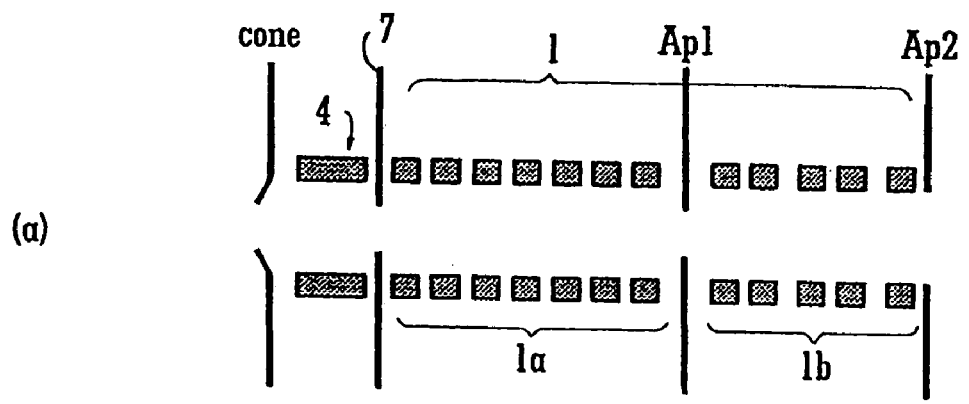
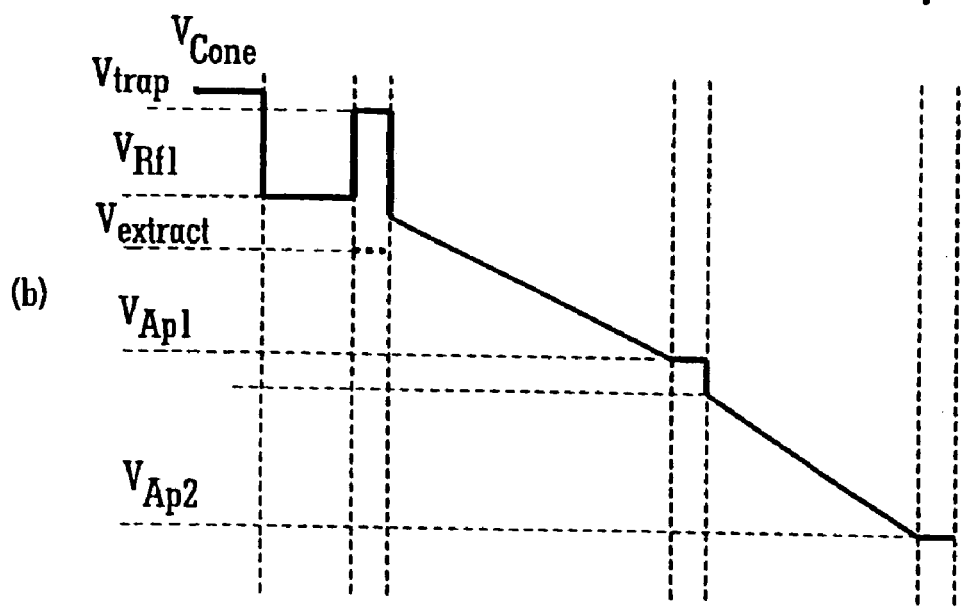
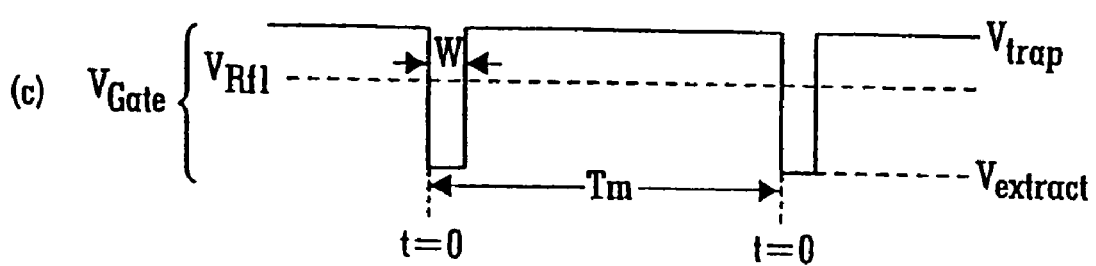
FIG. 7

MASS SPECTROMETER

CROSS REFERENCE TO RELATED APPLICATION

This application claims the benefit of the filing of U.S. Provisional Patent Application Ser. No. 60/477,054 filed Jun. 10, 2003.

BACKGROUND OF THE INVENTION

1. Field of the Invention

The present invention relates to a mass spectrometer and a method of mass spectrometry.

2. Discussion of the Prior Art

With the decoding of the 20–30,000 genes that compose the human genome, emphasis has switched to the identification of the translated gene products that comprise the proteome. Mass spectrometry has firmly established itself as the primary technique for identifying proteins due to its unparalleled speed, sensitivity and specificity. Strategies can involve either analysis of the intact protein, or more commonly digestion of the protein using a specific protease that cleaves at predictable residues along the peptide backbone. This provides smaller stretches of peptide sequence that are more amenable to analysis via mass spectrometry.

The mass spectrometry technique providing the highest degree of specificity and sensitivity is Electrospray ionisation ("ESI") interfaced to a tandem mass spectrometer. These experiments involve separation of the complex digest mixture by microcapillary liquid chromatography with on-line mass spectral detection using automated acquisition modes whereby conventional MS and MS/MS spectra are collected in a data dependant manner. This information can be used directly to search databases for matching sequences leading to identification of the parent protein. This approach can be used to identify proteins that are present at low endogenous concentrations. However, often the limiting factor for identification of the protein is not the quality of the MS/MS spectrum produced but is the initial discovery of the multiply charged peptide precursor ion in the MS mode. This is due to the level of background chemical noise, largely singly charged in nature, which may be produced in the ion source of the mass spectrometer. FIG. 1 shows a typical conventional mass spectrum and illustrates how doubly charged species may be obscured amongst a singly charged background. A method whereby the chemical noise (which is predominantly due to singly charged ions) is reduced so that the mass spectrometer can more easily target peptide related ions would be highly advantageous for the study of protein digests. In the field of proteomics the limiting factor in the identification of proteins is often not the inability to generate adequate fragmentation (or "MS/MS") data but the inability to recognise peptide precursor ions in mass spectra. A large proportion of the peptide product ions from a tryptic digest of a mixture of proteins will be multiply charged and this may be used as a means of recognising such peptide product ions. However, at relatively low levels these multiply charged peptide product ions may be relatively or substantially obscured due to the presence of more intense singly charged chemical background ions.

A known method used to favour the detection of multiply charged species over singly charged species is to use an Electrospray ionisation orthogonal acceleration Time of Flight mass analyser ("ESI-oaTOF"). The orthogonal acceleration Time of Flight mass analyser counts the arrival of ions using a Time to Digital Converter ("TDC") which has a discriminator threshold. The voltage pulse of a single ion must be high enough to trigger the discriminator and so register the arrival of an ion. The detector producing the voltage may be an electron multiplier or a Microchannel Plate detector ("MCP"). These detectors are charge sensitive so the size of signal they produce increases with increasing charge state. Discrimination in favour of higher charge states can be accomplished by increasing the discriminator voltage level, lowering the detector gain, or a combination of both. FIG. 2A shows a mass spectrum obtained with normal detector gain and FIG. 2B shows a comparable mass spectrum obtained with a reduced detector gain. A significant disadvantage of lowering the detector gain (or of increasing the discriminator level) is that the sensitivity is lowered. As can be seen from the ordinate axes of FIGS. 2A and 2B, the sensitivity is reduced by a factor of approximately x4 when a lower detector gain is employed. Using this method it is also impossible to pick out an individual charge state. Instead, the best that can be achieved is a reduction of the efficiency of detection of lower charge states with respect to higher charge states.

Another ionisation technique that has been recently coupled to tandem mass spectrometers for biological mass spectrometry is Matrix Assisted Laser Desorption Ionisation ("MALDI"). When a MALDI ion source is used high levels of singly charged matrix related ions and chemical noise are generated which make it difficult to identify candidate peptide ions.

It is therefore desired to provide an improved mass spectrometer and method of mass spectrometry which does not suffer from some or all of the disadvantages of the prior art.

SUMMARY OF THE INVENTION

According to an aspect of the present invention there is provided a mass spectrometer comprising:

an ion mobility separator for separating ions according to their ion mobility so that ions emerge from the ion mobility separator over different time intervals;

a Time of Flight mass analyser comprising a flight region, the Time of Flight mass analyser arranged to mass analyse at least some of the ions of a first group of ions which emerge from the ion mobility separator during a first time interval; and processing means arranged to:

(i) produce a first mass spectral set of data including data corresponding to the time of flight of at least some of the ions of the first group of ions through the flight region; and (ii) process the first mass spectral set of data to form a first processed mass spectral set of data wherein the intensity or significance of ions having a first undesired charge state is reduced relative to ions having a second different desired charge state.

Preferably, the intensity of ions having a first undesired charge state is attenuated, preferably significantly attenuated, whereas the intensity of ions having a second desired charge state is preferably unaffected.

Ions are preferably pulsed at least x times into the ion mobility separator and wherein the first mass spectral set of data is a composite set of mass spectral data obtained by summing at least x sets of mass spectral data, wherein the x sets of mass spectral data relate to separate pulses of ions. The value x may lie within the range 1–10, 10–20, 20–30, 30–40, 40–50, 50–60, 60–70, 70–80, 80–90, 90–100, 100–150, 150–200, 200–250, 250–300, 300–350, 350–400, 400–450, 450–500 or >500.

At least some of the ions of at least n further groups of ions which emerge from the ion mobility separator during at least n further time intervals may be mass analysed in use with the Time of Flight mass analyser. The processing means preferably produces at least n further mass spectral sets of data each including data corresponding to the time of flight of at least some of the ions of the at least n further groups of ions through the flight region.

Ions are preferably pulsed at least x times into the ion mobility separator and wherein the n further mass spectral sets of data are composite sets of mass spectral data wherein each composite set of mass spectral data is obtained by summing at least x sets of mass spectral data, wherein the x sets of mass spectral data relate to separate pulses of ions.

The processing mean preferably processes the at least n further mass spectral sets of data to form at least n further processed mass spectral sets of data wherein the intensity or significance of ions having the first undesired charge state is reduced relative to ions having the second desired charge state.

The processing means preferably processes the first and/or n further mass spectral sets of data by attenuating the intensity or significance of ions having a flight time less than a minimum flight time.

Alternatively, the processing means may process the first and/or n further mass spectral sets of data by attenuating the intensity or significance of ions having a flight time less than a minimum flight time and greater than a maximum flight time.

According to another embodiment the processing means may process the first and/or n further mass spectral sets of data by attenuating the intensity or significance of ions having a flight time greater than a maximum flight time.

The value n may fall within the range 1–10, 10–20, 20–30, 30–40, 40–50, 50–60, 60–70, 70–80, 80–90, 90–100, 100–110, 110–120, 120–130, 130–140, 140–150, 150–160, 160–170, 170–180, 180–190, 190–200, 200–250, 250–300, 350–400, 400–450, 450–500 and >500.

Preferably, the minimum flight time and/or the maximum flight time is progressively increased or decreased when processing mass spectral sets of data which were obtained in subsequent time intervals. The minimum flight time and/or maximum flight time is preferably progressively increased or decreased in: (i) a substantially continuous manner; (ii) a substantially stepped manner; (iii) a substantially linear manner; (iv) a substantially non-linear manner; or (v) a substantially exponential manner.

The processing means preferably forms a mass spectrum using the first processed mass spectral set of data. The processing means preferably forms a mass spectrum using the at least n further processed mass spectral sets of data.

According to another aspect of the present invention there is provided a mass spectrometer comprising:
an ion mobility separator for separating ions according to their ion mobility so that ions emerge from the ion mobility separator over different time intervals;
a Time of Flight mass analyser comprising a flight region, the Time of Flight mass analyser arranged to mass analyse at least some of the ions which emerge from the ion mobility separator; and processing means arranged to:
(i) produce a first ion mobility set of data including data corresponding to the drift time of at least some ions through the ion mobility separator; and (ii) process the first ion mobility set of data to form a first processed ion mobility set of data wherein the intensity or significance of ions having a first undesired charge state is reduced relative to ions having a second different desired charge state.

Preferably, the first ion mobility set of data is a composite set of ion mobility data obtained by summing a plurality of sets of ion mobility data.

The processing means preferably processes the first and/or a plurality of further ion mobility sets of data by attenuating the intensity or significance of ions having a drift time through the ion mobility separator greater than a maximum drift time.

Alternatively, the processing means preferably processes the first and/or a plurality of further ion mobility sets of data by attenuating the intensity or significance of ions having a drift time through the ion mobility separator less than a minimum drift time and greater than a maximum drift time.

According to another embodiment the processing means processes the first and/or a plurality of further ion mobility sets of data by attenuating the intensity or significance of ions having a drift time through the ion mobility separator less than a minimum drift time.

The minimum drift time and/or the maximum drift time is progressively increased or decreased when processing consecutive, following or neighbouring sets of ion mobility data.

The minimum drift time and/or maximum drift time is progressively increased or decreased in: (i) a substantially continuous manner; (ii) a substantially stepped manner; (iii) a substantially linear manner; (iv) a substantially non-linear manner; or (v) a substantially exponential manner.

The processing means preferably forms a mass spectrum using the first processed ion mobility set of data. The processing means preferably forms a mass spectrum using a plurality of further processed ion mobility sets of data.

The first charge state preferably comprises singly charged ions. The second charge state preferably comprises multiply charged ions, for example doubly charged ions, triply charged ions, quadruply charged ions or ions having five or more charges.

According to one embodiment the ion mobility separator comprises a plurality of electrodes, each electrode having an aperture through which ions are transmitted in use, wherein a DC voltage gradient is maintained across at least a portion of the ion mobility separator and at least some of the electrodes are connected to an AC or RF voltage supply.

The ion mobility separator preferably comprises; an upstream section comprising a first plurality of electrodes having apertures arranged in a vacuum chamber; and a downstream section comprising a second plurality of electrodes having apertures arranged in a further vacuum chamber, the vacuum chamber being separated by a differential pumping aperture.

At least some of the electrodes in the upstream section are preferably supplied with an AC or RF voltage having a frequency within the range 0.1–3.0 MHz, preferably 0.5–1.1 MHz, more preferably approximately 780 kHz. The upstream section is preferably maintained at a pressure within the range 0.1–10 mbar, preferably 1 mbar. At least some of the electrodes in the downstream section are preferably supplied with an AC or RF voltage having a frequency within the range 0.1–3.0 MHz, preferably 1.8–2.4 MHz, more preferably 2.1 MHz. The downstream section is preferably maintained at a pressure within the range $10^{-3}$–$10^{-2}$ mbar. According to an embodiment a first DC voltage gradient is maintained across at least a portion of the upstream section and a second DC voltage gradient is maintained across at least a portion of the downstream section, the first DC voltage gradient being greater than the second DC voltage gradient. Either voltage gradient does not necessarily have to be linear and indeed a stepped voltage gradient is particularly preferred.

At least 60%, 65%, 70%, 75%, 80%, 85%, 90%, 95% of the electrodes preferably have apertures which are of substantially the same size or area.

According to another embodiment the ion mobility separator comprises a segmented rod set and wherein a DC voltage gradient is maintained across at least a portion of the ion mobility separator.

According to another embodiment the ion mobility separator comprises a drift tube together with one or more electrodes for maintaining an axial DC voltage gradient along at least a portion of the drift tube.

According to another embodiment the ion mobility separator comprises a plurality of electrodes wherein in use one or more transient DC voltages or one or more transient DC voltage waveforms are progressively applied to the electrodes so that at least some ions having a first ion mobility are separated from other ions having a second different ion mobility.

The one or more transient DC voltages or the one or more transient DC voltage waveforms are preferably such that at least 10%, 20%, 30%, 40%, 50%, 60%, 70%, 80%, 90% or 95% of the ions having the first ion mobility are moved along the ion mobility separator with a higher velocity than the ions having the second ion mobility.

According to another embodiment the ion mobility separator comprises a plurality of electrodes wherein in use one or more transient DC voltages or one or more transient DC voltage waveforms are progressively applied to the electrodes so that ions are moved towards a region of the ion mobility separator wherein at least one electrode has a potential such that at least some ions having a first ion mobility will pass across the potential whereas at least some other ions having a second different ion mobility will not pass across the potential.

The one or more transient DC voltages or the one or more transient DC voltage waveforms are preferably such that at least 10%, 20%, 30%, 40%, 50%, 60%, 70%, 80%, 90% or 95% of the ions having the first ion mobility pass across the potential. The one or more transient DC voltages or the one or more transient DC voltage waveforms are preferably such that at least 10%, 20%, 30%, 40%, 50%, 60%, 70%, 80%, 90% or 95% of the ions having the second ion mobility will not pass across the potential. Preferably, the one or more transient DC voltages or the one or more transient DC voltage waveforms are such that at least 10%, 20%, 30%, 40%, 50%, 60%, 70%, 80%, 90% or 95% of the ions having the first ion mobility exit the ion mobility separator substantially before ions having the second ion mobility.

A majority of the ions having the first ion mobility preferably exit the ion mobility separator a time t before a majority of the ions having the second ion mobility exit the ion mobility separator, wherein t falls within a range of <1 $\mu$s, 1–10 $\mu$s, 10–50 $\mu$s, 50–100 $\mu$s, 100–200 $\mu$s, 200–300 $\mu$s, 300–400 $\mu$s, 400–500 $\mu$s, 500–600 $\mu$s, 600–700 $\mu$s, 700–800 $\mu$s, 800–900 $\mu$s, 900–1000 $\mu$s, 1.0–1.1 ms, 1.1–1.2 ms, 1.2–1.3 ms, 1.3–1.4 ms, 1.4–1.5 ms, 1.5–1.6 ms, 1.6–1.7 ms, 1.7–1.8 ms, 1.8–1.9 ms, 1.9–2.0 ms, 2.0–2.5 ms, 2.5–3.0 ms, 3.0–3.5 ms, 3.5–4.0 ms, 4.0–4.5 ms, 4.5–5.0 ms, 5–10 ms, 10–15 ms, 15–20 ms, 20–25 ms or 25–30 ms.

According to another preferred embodiment the ion mobility separator comprises a plurality of electrodes wherein in use one or more transient DC voltages or one or more transient DC voltage waveforms are progressively applied to the electrodes so that; (i) ions are moved towards a region of the ion mobility separator wherein at least one electrode has a first potential such that at least some ions having first and second different ion mobilities will pass across the first potential whereas other ions having a third different ion mobility will not pass across the first potential; and then (ii) ions having the first and second ion mobilities are moved towards a region of the ion mobility separator wherein at least one electrode has a second potential such that at least some ions having the first ion mobility will pass across the second potential whereas other ions having the second different ion mobility will not pass across the second potential.

The one or more transient DC voltages may create a potential hill or barrier, a potential well, a combination of a potential hill or barrier and a potential well, multiple potential hills or barriers, multiple potential wells, or a combination of multiple potential hills or barriers and multiple potential wells. The one or more transient DC voltage waveforms may comprise a repeating waveform, for example a square wave.

The one or more transient DC voltage waveforms may create a plurality of potential peaks or wells separated by intermediate regions. Preferably, the DC voltage gradient in the intermediate regions is non-zero, is positive, is negative, is linear, is non-linear, or increases exponentially, or decreases exponentially.

The amplitude of the potential peaks or wells may remain substantially constant, become progressively larger or smaller, or may increase or decrease either linearly or non-linearly.

An axial DC voltage gradient maybe maintained along at least a portion of the length of the ion mobility separator and wherein the axial voltage gradient varies with time.

The ion mobility separator may comprise 3, 4, 5, 6, 7, 8, 9, 10, 11, 12, 13, 14, 15, 16, 17, 18, 19, 20, 21, 22, 23, 24, 25, 26, 27, 28, 29, 30 or >30 segments, wherein each segment comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or >30 electrodes and wherein the electrodes in a segment are maintained at substantially the same DC potential.

A plurality of segments may be maintained at substantially the same DC potential. Each segment may be maintained at substantially the same DC potential as the subsequent yth segment wherein y is 3, 4, 5, 6, 7, 8, 9, 10, 11, 12, 13, 14, 15, 16, 17, 18, 19, 20, 21, 22, 23, 24, 25, 26, 27, 28, 29, 30 or >30.

Ions are preferably confined radially within the ion mobility separator by an AC or RF electric field. Ions may be radially confined within the ion mobility separator in a pseudo-potential well and may be moved axially along the ion mobility separator by a real potential barrier or well.

According to a less preferred embodiment one or more AC or RF voltage waveforms may be applied to at least some of the electrodes so that ions are urged along at least a portion of the length of the ion mobility separator.

The minimum, average or maximum transit time of ions through the ion mobility separator may be less than or equal to 20 ms, 10 ms, 5 ms, 1 ms or 0.5 ms.

The ion mobility separator may be maintained in use at a pressure selected from the group consisting of: (i) greater than or equal to 0.0001 mbar; (ii) greater than or equal to 0.0005 mbar; (iii) greater than or equal to 0.001 mbar; (iv) greater than or equal to 0.005 mbar; (v) greater than or equal to 0.01 mbar; (vi) greater than or equal to 0.05 mbar; (vii)

greater than or equal to 0.1 mbar; (viii) greater than or equal to 0.5 mbar; (ix) greater than or equal to 1 mbar; (x) greater than or equal to 5 mbar; and (xi) greater than or equal to 10 mbar.

The ion mobility separator may be maintained in use at a pressure selected from the group consisting of: (i) less than or equal to 10 mbar; (ii) less than or equal to 5 mbar; (iii) less than or equal to 1 mbar; (iv) less than or equal to 0.5 mbar; (v) less than or equal to 0.1 mbar; (vi) less than or equal to 0.05 mbar; (vii) less than or equal to 0.01 mbar; (viii) less than or equal to 0.005 mbar; (ix) less than or equal to 0.001 mbar; (x) less than or equal to 0.0005 mbar; and (xi) less than or equal to 0.0001 mbar.

The ion mobility separator may be maintained, in use, at a pressure selected from the group consisting of: (i) between 0.0001 and 10 mbar; (ii) between 0.0001 and 1 mbar; (iii) between 0.0001 and 0.1 mbar; (iv) between 0.0001 and 0.01 mbar; (v) between 0.0001 and 0.001 mbar; (vi) between 0.001 and 10 mbar; (vii) between 0.001 and 1 mbar; (viii) between 0.001 and 0.1 mbar; (ix) between 0.001 and 0.01 mbar; (x) between 0.01 and 10 mbar; (xi) between 0.01 and 1 mbar; (xii) between 0.01 and 0.1 mbar; (xiii) between 0.1 and 10 mbar; (xiv) between 0.1 and 1 mbar; and (xv) between 1 and 10 mbar.

The ion mobility separator may be maintained, in use, at a pressure such that a viscous drag is imposed upon ions passing through the ion mobility separator.

The one or more transient DC voltages or the one or more transient DC voltage waveforms may be initially provided at a first axial position and are then subsequently provided at a second, then third different axial positions along the ion mobility separator.

The one or more transient DC voltages or the one or more transient DC voltage waveforms may move from one end of the ion mobility separator to another end of the ion mobility separator so that at least some ions are urged along the ion mobility separator.

The one or more transient DC voltages or the one more transient DC voltage waveforms may move along the ion mobility separator with a velocity of 10–250 m/s, 250–500 m/s, 500–750 m/s, 750–1000 m/s, 1000–1250 m/s, 1250–1500 m/s, 1500–1750 m/s, 1750–2000 m/s, 2000–2250, 2250–2500 m/s, 2500–2750 m/s, 2750–3000 m/s or >3000 m/s.

Two or more transient DC voltages or two or more transient DC voltage waveforms may pass simultaneously along the ion mobility separator.

According to an embodiment a continuous beam of ions may be received at an entrance to the ion mobility separator. Alternatively, packets of ions may be received at an entrance to the ion mobility separator.

The ion mobility separator may comprise 10–20, 20–30, 30–40, 40–50, 50–60, 60–70, 70–80, 80–90, 90–100, 100–110, 110–120, 120–130, 130–140, 140–150 or more than 150 electrodes. At least 10%, 20%, 30%, 40%, 50%, 60%, 70%, 80%, 90%, or 95% of the electrodes forming the ion mobility separator are preferably connected to both a DC and an AC or RF voltage supply. Axially adjacent electrodes of the ion mobility separator are preferably supplied with AC or RF voltages having a phase difference of 180%.

The mass spectrometer may comprise an Electrospray ("ESI") ion source, an Atmospheric Pressure Chemical Ionisation ("APCI") ion source, an Atmospheric Pressure Photo Ionisation ("APPI") ion source, a Matrix Assisted Laser Desorption Ionisation ("MALDI") ion source, a Laser Desorption Ionisation ("LDI") ion source, an Inductively Coupled Plasma ("ICP") ion source, an Electron Impact ("EI") ion source, a Chemical Ionisation ("CI") ion source, a Fast Atom Bombardment ("FAB") ion source, a Liquid Secondary Ion Mass Spectrometry ("LSIMS") ion source, a Field Ionisation ("FI") ion source or a Field Desorption ("FD") ion source.

In a less preferred embodiment the mass spectrometer may comprise a Fourier Transform mass spectrometer or a Fourier Transform Ion Cyclotron Resonance mass spectrometer. The ion source may be a continuous ion source or a pulsed ion source. The ion source may be coupled to a Gas Chromatograph ("GC") or a Liquid Chromatograph ("LC").

The Time of Flight mass analyser preferably comprises an injection electrode for injecting at least some ions in a direction substantially orthogonal to or parallel with an axis along which ions initially enter the Time of Flight mass analyser.

An ion trap upstream of the Time of Flight mass analyser may be provided for storing and periodically releasing ions into the Time of Flight mass analyser. Similarly, an ion trap preferably upstream of the ion mobility separator may be provided for storing ions and periodically releasing ions to the ion mobility separator.

A collision cell may be provided downstream of the ion mobility separator wherein in one mode of operation at least some ions entering the collision cell are caused to fragment. A mass filter, preferably a quadruple mass filter, may also be provided downstream of the ion mobility separator and preferably upstream of a collision cell (if provided).

According to a less preferred embodiment instead of post-processing a complete set of mass spectral data, the mass spectral data may be selectively recorded in the first place.

According to another aspect of the present invention there is provided a mass spectrometer comprising:

an ion mobility separator for separating ions according to their ion mobility so that ions emerge from the ion mobility separator over different time intervals;

a Time of Flight mass analyser comprising a flight region, the Time of Flight mass analyser arranged to mass analyse at least some of the ions of a first group of ions which emerge from the ion mobility separator during a first time interval; and processing means arranged to record the time of flight of some of the ions of the first group of ions through the flight region to form a first mass spectral set of data wherein the intensity or significance of ions having a flight time less than a minimum flight time is reduced.

According to another aspect of the present invention there is provided a mass spectrometer comprising:

an ion mobility separator for separating ions according to their ion mobility so that ions emerge from the ion mobility separator over different time intervals;

a Time of Flight mass analyser comprising a flight region, the Time of Flight mass analyser arranged to mass analyse at least some of the ions of a first group of ions which emerge from the ion mobility separator during a first time interval; and processing means arranged to record the time of flight of some of the ions of the first group of ions through the flight region to form a first mass spectral set of data wherein the intensity or significance of ions having a flight time less than a minimum flight time and greater than a maximum flight time is reduced.

According to another aspect of the present invention there is provided a mass spectrometer comprising:
- an ion mobility separator for separating ions according to their ion mobility so that ions emerge from the ion mobility separator over different time intervals;
- a Time of Flight mass analyser comprising a flight region, the Time of Flight mass analyser arranged to mass analyse at least some of the ions of a first group of ions which emerge from the ion mobility separator during a first time interval; and
- processing means arranged to record the time of flight of some of the ions of the first group of ions through the flight region to form a first mass spectral set of data wherein the intensity or significance of ions having a flight time greater than a maximum flight time is reduced.

According to another aspect of the present invention there is provided a mass spectrometer comprising;
- an ion mobility separator for separating ions according to their ion mobility so that ions emerge from the ion mobility separator over different time intervals;
- a Time of Flight mass analyser comprising a flight region, the Time of Flight mass analyser arranged to mass analyse at least some of the ions which emerge from the ion mobility separator; and
- processing means arranged to record the drift time of at least some of the ions which emerge from the ion mobility separator to form a first ion mobility set of data wherein the intensity or significance of ions having a drift time through the ion mobility separator greater than a maximum drift time is reduced.

According to another aspect of the present invention there is provided a mass spectrometer comprising:
- an ion mobility separator for separating ions according to their ion mobility so that ions emerge from the ion mobility separator over different time intervals;
- a Time of Flight mass analyser comprising a flight region, the Time of Flight mass analyser arranged to mass analyse at least some of the ions which emerge from the ion mobility separator; and
- processing means arranged to record the drift time of at least some of the ions which emerge from the ion mobility separator to form a first ion mobility set of data wherein the intensity or significance of ions having a drift time through the ion mobility separator less than a minimum drift time and greater than a maximum drift time is reduced.

According to another aspect of the present invention there is provided a mass spectrometer comprising:
- an ion mobility separator for separating ions according to their ion mobility so that ions emerge from the ion mobility separator over different time intervals;
- a Time of Flight mass analyser comprising a flight region, the Time of Flight mass analyser arranged to mass analyse at least some of the ions which emerge from the ion mobility separator; and
- processing means arranged to record the drift time of at least some of the ions which emerge from the ion mobility separator to form a first ion mobility set of data wherein the intensity or significance of ions having a drift time through the ion mobility separator less than a minimum drift time is reduced.

According to another aspect of the present invention there is provided a method of mass spectrometry comprising:
- separating ions according to their ion mobility in an ion mobility separator so that ions emerge from the ion mobility separator over different time intervals;
- mass analysing at least some of the ions of a first group of ions which emerge from the ion mobility separator during a first time interval with a Time of Flight mass analyser, the Time of Flight mass analyser comprising a flight region;
- producing a first mass spectral set of data including data corresponding to the time of flight of at least some of the ions of the first group of ions through the flight region; and
- processing the first mass spectral set of data to form a first processed mass spectral set of data wherein the intensity or significance of ions having a first undesired charge state is reduced relative to ions having a second different desired charge state.

According to another aspect of the present invention there is provided a method of mass spectrometry comprising:
- separating ions according to their ion mobility in an ion mobility separator so that ions emerge from the ion mobility separator over different time intervals;
- passing at least some of the ions of a first group of ions which emerge from the ion mobility separator during a first time interval to a Time of Flight mass analyser, the Time of Flight mass analyser comprising-a flight region; and
- recording the time of flight of some of the ions of the first group of ions through the flight region to form a first mass spectral set of data wherein the intensity or significance of ions having a flight time less than a minimum flight time is reduced.

According to another aspect of the present invention there is provided a method of mass spectrometry comprising:
- separating ions according to their ion mobility in an ion mobility separator so that ions emerge from the ion mobility separator over different time intervals;
- passing at least some of the ions of a first group of ions which emerge from the ion mobility separator during a first time interval to a Time of Flight mass analyser, the Time of Flight mass analyser comprising a flight region; and
- recording the time of flight of some of the ions of the first group of ions through the flight region to form a first mass spectral set of data wherein the intensity or significance of ions having a flight time less than a minimum flight time and greater than a maximum flight time is reduced.

According to another aspect of the present invention there is provided a method of mass spectrometry comprising:
- separating ions according to their ion mobility in an ion mobility separator so that ions emerge from the ion mobility separator over different time intervals;
- passing at least some of the ions of a first group of ions which emerge from the ion mobility separator during a first time interval to a Time of Flight mass analyser, the Time of Flight mass analyser comprising a flight region; and
- recording the time of flight of some of the ions of the first group of ions through the flight region to form a first mass spectral set of data wherein the intensity or significance of ions having a flight time greater than a maximum flight time is reduced.

According to another aspect of the present invention there is provided a method of mass spectrometry comprising:
- separating ions according to their ion mobility in an ion mobility separator so that ions emerge from the ion mobility separator over different time intervals;

passing at least some of the ions which emerge from the ion mobility separator to a Time of Flight mass analyser, the Time of Flight mass analyser comprising a flight region; and recording the ion mobility of the ions of at least some of the ions to form a first ion mobility set of data wherein the intensity or significance of ions having a drift time through the ion mobility separator greater than a maximum drift time is reduced.

According to another aspect of the present invention there is provided a method of mass spectrometry comprising:

separating ions according to their ion mobility in an ion mobility separator so that ions emerge from the ion mobility separator over different time intervals;

passing at least some of the ions which emerge from the ion mobility separator to a Time of Flight mass analyser, the Time of Flight mass analyser comprising a flight region; and recording the ion mobility of the ions of at least some of the ions to form a first ion mobility set of data wherein the intensity or significance of ions having a drift time through the ion mobility separator less than a minimum drift time and greater than a maximum drift time is reduced.

According to another aspect of the present invention there is provided a method of mass spectrometry comprising:

separating ions according to their ion mobility in an ion mobility separator so that ions emerge from the ion mobility separator over different time intervals;

passing at least some of the ions which emerge from the ion mobility separator to a Time of Flight mass analyser, the Time of Flight mass analyser comprising a flight region; and recording the ion mobility of the ions of at least some of the ions to form a first ion mobility set of data wherein the intensity or significance of ions having a drift time through the ion mobility separator less than a minimum drift time is reduced.

According to another aspect of the present invention there is provided a method of mass spectrometry comprising obtaining mass spectral data or ion mobility data and processing the data to exclude ions having an undesired charge state.

An ion trap may be provided upstream of the flight region. This ion trap is separate to an ion trap which may be provided preferably upstream of the ion mobility separator. The ion trap may preferably store and periodically release ions so that a pulsed (rather than a continuous) source of ions is admitted or otherwise inputted in to the flight region. The injection electrode is arranged to inject ions a predetermined period of time after ions have first been released from the ion trap upstream of the drift region. The period of time is set so that only ions having a desired mass to charge ratio or a mass to charge ratio within a desired range are substantially injected by the injection electrode in an orthogonal direction and are hence onwardly transmitted.

Ions in an ion mobility separator (which may also be referred to as an ion mobility spectrometer) are preferably subjected to an electric field in the presence of a buffer gas so that different ion species will acquire different velocities as they pass through the ion mobility separator. The velocity of the ion passing through the ion mobility separator will depend upon their mobility which itself depends upon the mass and charge of the particular ion. Ions having a relatively high ion mobility will acquire a relatively higher velocity compared with ions having a relatively low ion mobility. Similarly, relatively heavy singly charged ions will have lower ion mobilities (and hence lower velocities) than lighter singly charged ions.

According to a more preferred embodiment the ion mobility separator may comprise a plurality of electrodes having apertures through which ions are transmitted in use. A constant axial electric field gradient may be maintained along at least a portion of the length of the ion mobility separator.

According to another embodiment, one or more transient DC voltages or one or more DC voltage waveforms may be applied to the electrodes comprising the ion mobility separator so that ions having a particular ion mobility are preferentially swept along the ion mobility separator whilst other ions will take longer to emerge from the ion mobility separator. The ion mobility separator may trap ions both radially and axially within the ion mobility separator so that ions having a desired ion mobility are ejected from the ion mobility separator whereas all other ions will remain effectively trapped within the ion mobility separator.

A Time of Flight mass spectrometer is placed downstream of the ion mobility separator to analyse the ions emerging from the ion mobility separator. The Time of Flight mass analyser may comprise either an axial or an orthogonal acceleration Time of Flight mass analyser, Time of Flight mass analysis are parallel analysers that detect and analyse ions of all mobilities and charge states.

BRIEF DESCRIPTION OF THE DRAWINGS

Various embodiments of the present invention will now be described, by way of example only, and with reference to the accompanying drawings in which;

FIG. 2A shows a conventional mass spectrum obtained with normal detector gains and FIG. 2B shows a comparable mass spectrum obtained by lowering the detector gain;

FIG. 7A illustrates an ion mobility separator according to an embodiment, FIG. 7B illustrates the various DC voltages which may be applied to the ion mobility separator and other components, and FIG. 7C illustrates how the DC voltage applied to an ion gate upstream of the ion mobility separator may vary as a function of time to release ions into the ion mobility separator;

DETAILED DESCRIPTION OF THE PREFERRED EMBODIMENTS

Figure 1:
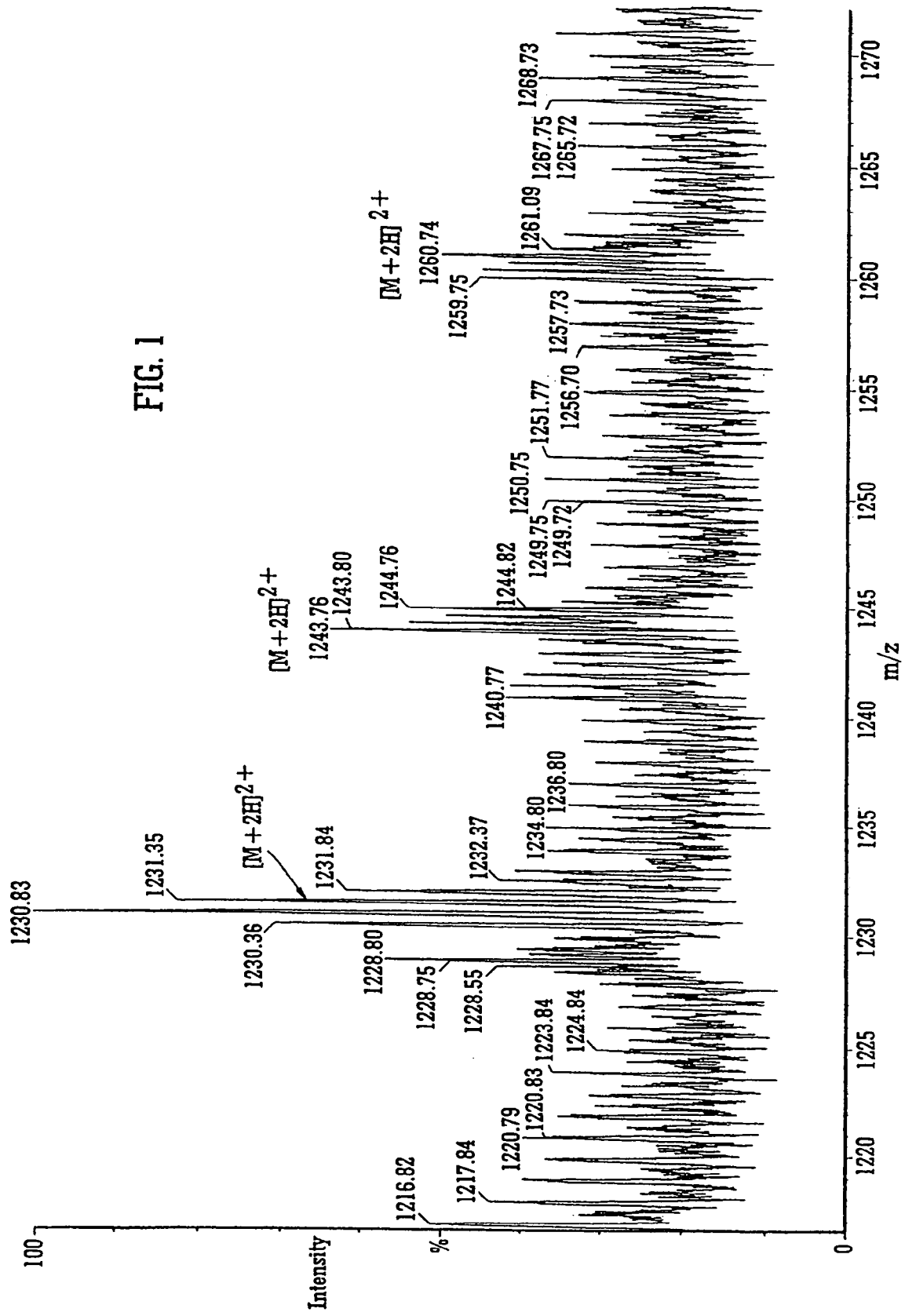
FIG. 1 shows a conventional mass spectrum.
Figure 3A:
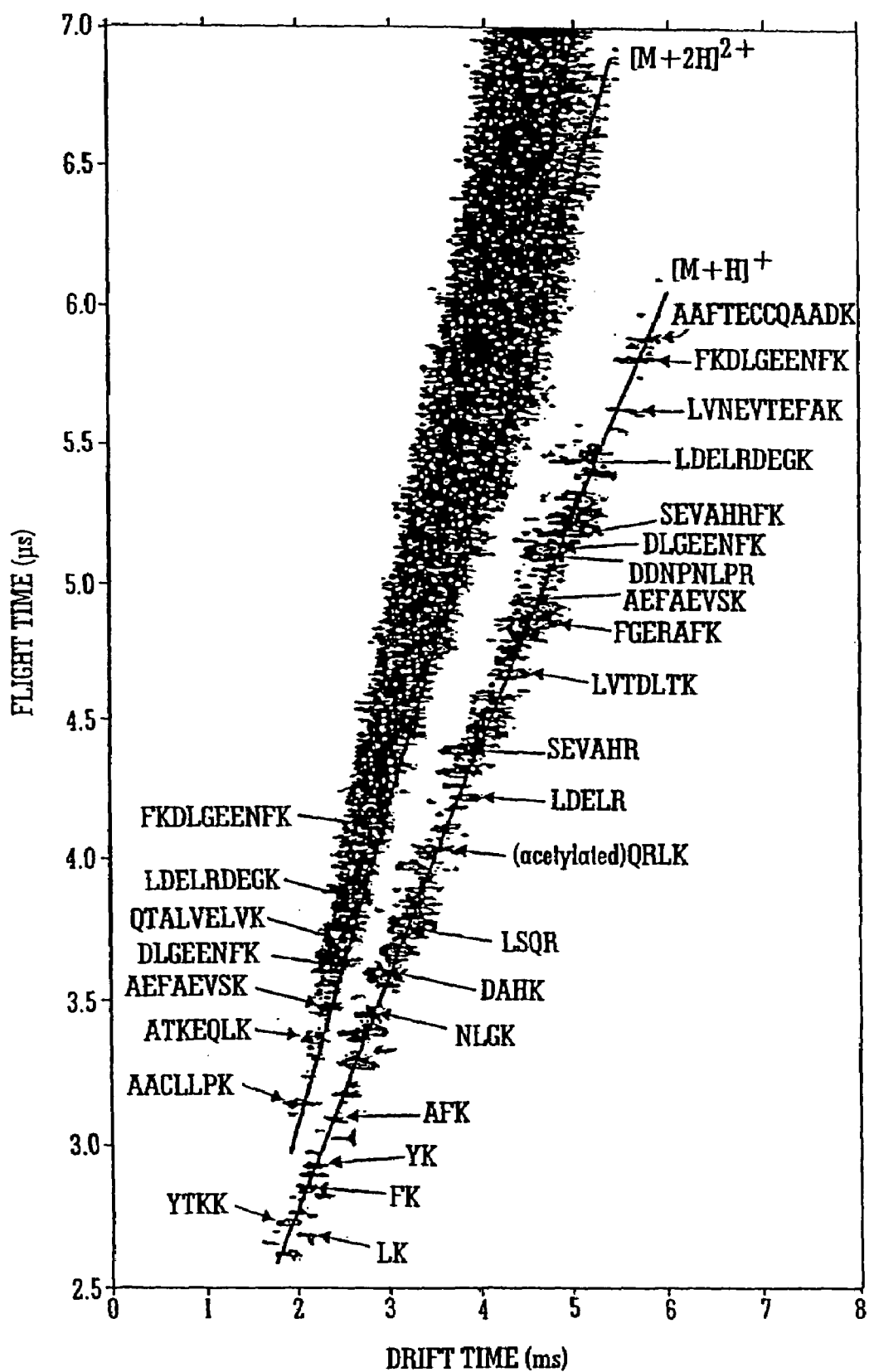
FIG. 3A shows the known relationship between flight time in a Time of Flight mass analyser versus drift time in an ion mobility separator for various singly and doubly charged ions.
Figure 3B:
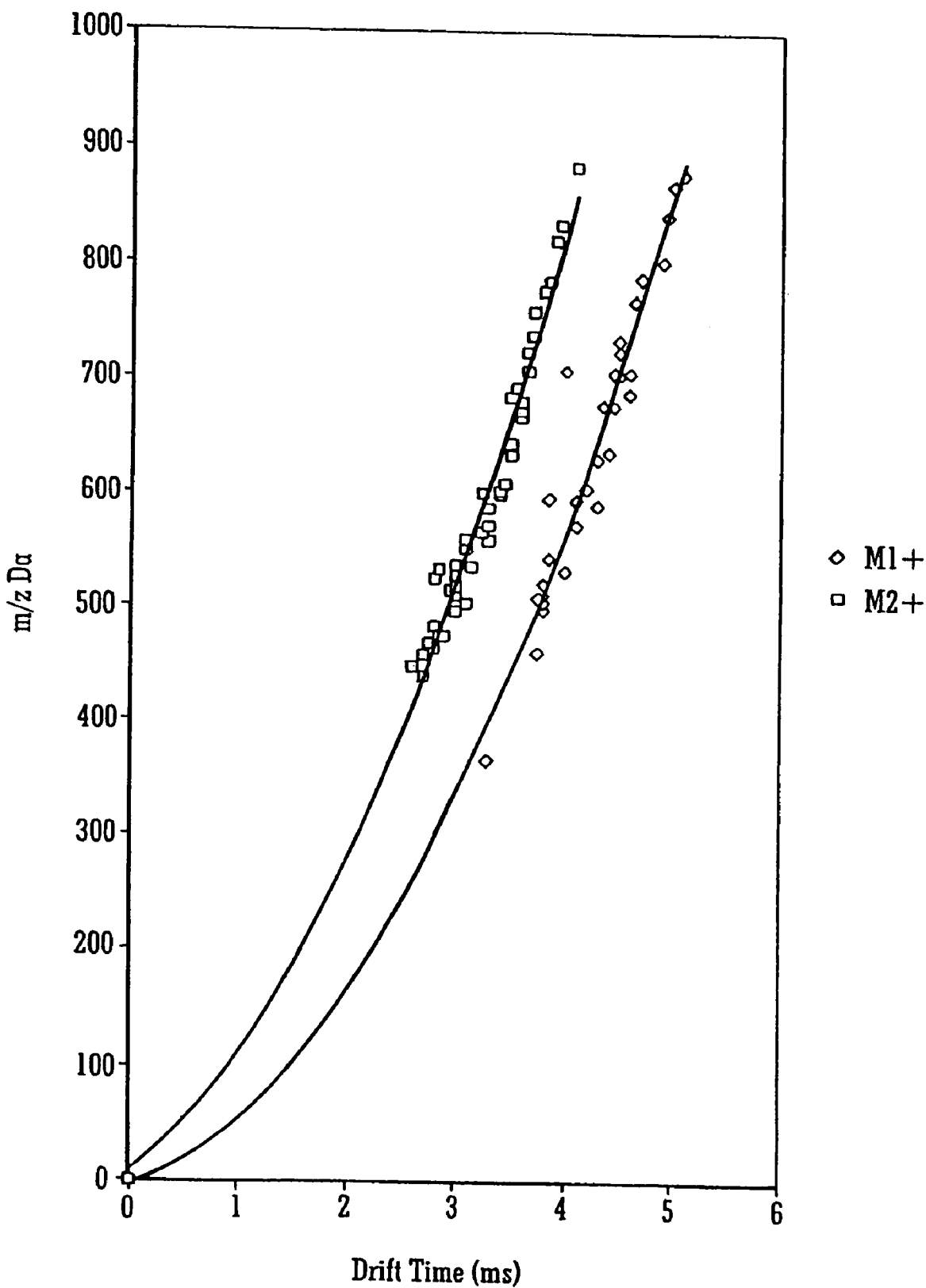
FIG. 3B shows an experimentally determined relationship between the mass to charge ratio of a sample of ions and their drift time through an ion mobility separator.

Various embodiments of the present invention will now be described. FIG. 3A shows the known relationship of flight time through a flight region of a Time of Flight mass analyser versus drift time through an ion mobility separator for various singly and doubly charged ions. An experimentally determined relationship between the mass to charge ratio of ions and their drift time through an ion mobility separator is shown in FIG. 3B. It can be seen that singly charged $[M+H]^+$ ions lie on a different characteristic line, curve or within a different characteristic band to that of doubly charged $[M+2H]^{2+}$ ions i.e. doubly charged ions have a shorter drift time through the ion mobility separator compared with singly charged ions having the same mass to charge ratio. Since the flight time of an ion through a Time of Flight mass analyser is related to the mass to charge ratio of the ion, then the y-axis can effectively be considered to correspond with the mass to charge ratio of ions. Accordingly, it can then be seen more clearly from FIG. 3B that singly charged ions having a particular mass to charge ratio will have a lower ion mobility (i.e. longer drift time through an ion mobility separator) than a doubly charged ion having substantially the same mass to charge ratio. This relationship can be represented by an empirically derived polynomial expression or other (e.g. exponential) relationship.

Figure 4:
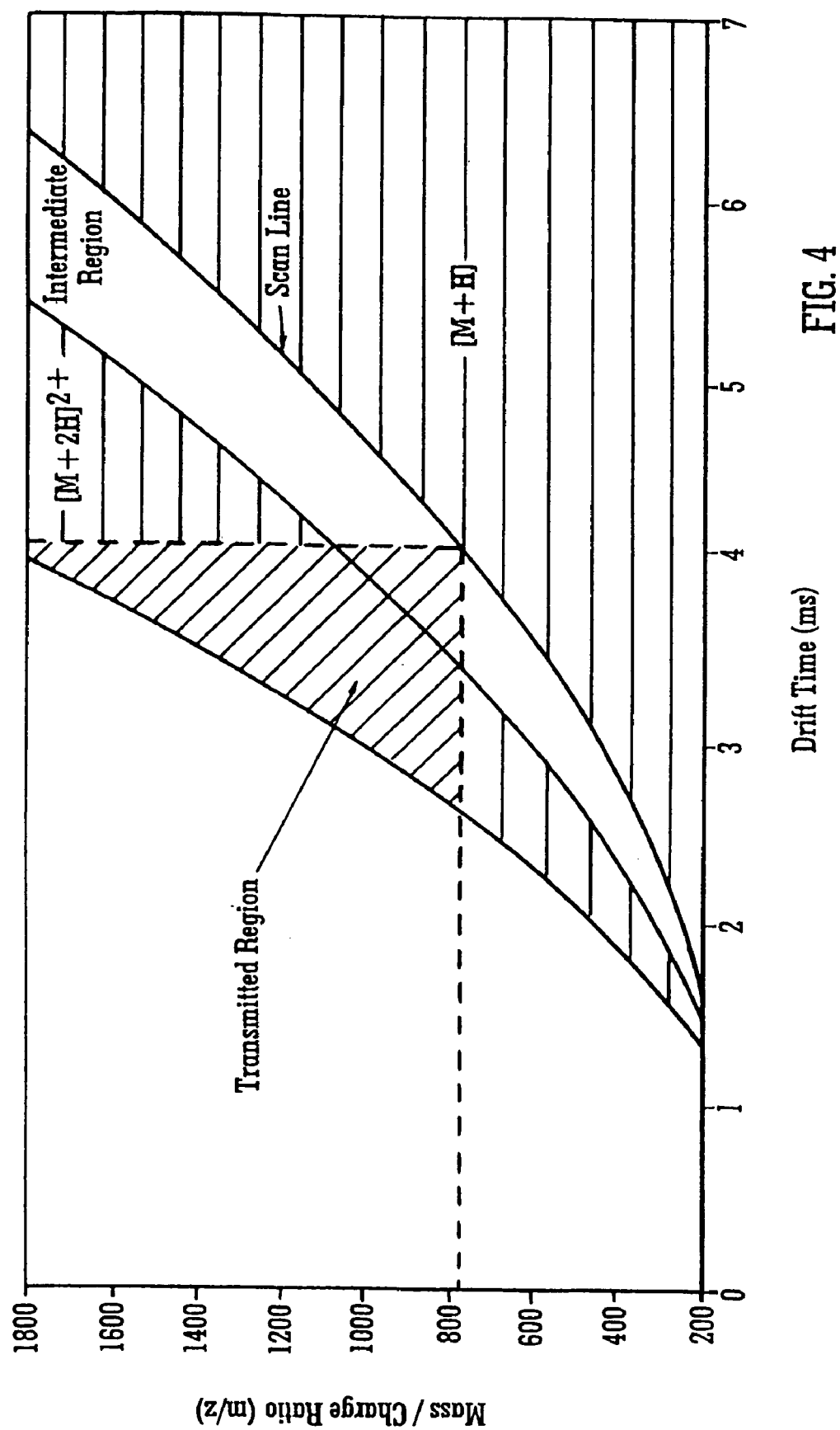
FIG. 4 illustrates the general principle of producing a mass spectrum wherein singly charged ions have been effectively excluded according to an embodiment of the present invention.

FIG. 4 illustrates how mass spectral data may be processed such that mass spectral data relating to ions having a particular charge state may be effectively selected to be used form the resultant mass spectrum whereas data relating to ions having an undesired charge state may be effectively rejected (or at least attenuated) and hence not be used to form the resultant mass spectrum. The known data of FIG. 3A and the experimentally derived data of FIG. 3B can be interpreted such that all ions having the same charge state can be considered to fall within a distinct region or band of a 2D plot of mass to charge ratio versus drift time through an ion mobility separator. In FIG. 4 singly and doubly charged ions are shown as falling within distinct bands with an intermediate region therebetween where very few ions of interest are to be found. Triply and quadruply charged ions etc. are not shown for ease of illustration only. The large area below the scan line can be considered to represent singly charged ions and the other area above it can be considered to represent doubly charged ions.

Considering FIG. 4, it can be seen that at a time around 4 ms after ions have first entered or been admitted to the drift region of the ion mobility separator, ions may be emerging from the ion mobility separator with various different mass to charge ratios. Those ions which emerge with a mass to charge ratio in the range of 1–790 are most likely to be singly charged ions whereas those ions emerging with a mass to charge ratio in the range 1070–1800 are most likely to be doubly charged ions. Very few, if any, ions will emerge at that point of time with a mass to charge ratio between 790–1070 (which corresponds with the intermediate region of the graph). Therefore, if the mass spectral data which has been obtained is post-processed so that mass spectral data which was obtained at this particular point in time is manipulated so that only data relating to ions having a mass to charge ratio>790 is used then it will be apparent that singly charged ions can be effectively excluded from the resultant composite mass spectrum. Advantageously, the mass spectrum will relate solely to doubly charged ions (and ions having a higher charge state). This is particularly advantageous in that it allows, for example, singly charged background ions to be effectively excluded from mass spectra and therefore the signal to noise ratio of, for example, multiply charged analyte ions amongst a background of singly charged ions can be significantly improved. Improvements in the signal to noise ratio of approximately 100 fold have been experimentally observed.

If the mass spectral data is post-processed so that the minimum mass to charge ratio of the mass spectral data which is retained (i.e. used to form the resultant mass spectrum) follows the "Scan Line" shown in FIG. 4 (i.e. if it tracks the upper predetermined mass to charge ratio for singly charged ions) then it will be appreciated that only mass spectral data relating to multiply charged ions will substantially be used to form the composite mass spectrum.

According to other embodiments the lower predetermined mass to charge ratio for doubly charged ions may be tracked. The cut-off mass to charge ratio may also lie for at least a portion of a processing cycle within the intermediate region which separates the regions comprising singly and doubly charged ions. The minimum cut-off mass to charge ratio applied to the mass spectral data may also vary in a predetermined or random manner between the upper threshold of the singly charged ion region, the intermediate region and the lower threshold of the doubly charged ion region. It will also be appreciated that according to less preferred embodiments, the minimum cut-off mass to charge ratio may fall for at least a portion of a processing cycle within the region considered to comprise either singly or doubly charged ions. In such circumstances, ions of a potentially unwanted charge State may still be included in the resultant mass spectrum, but the intensity and significance of such ions will nonetheless be reduced.

According to a preferred embodiment the minimum cut-off mass to charge ratio which may be applied to the obtained mass spectral data in order to filter out mass spectral data relating to ions having an undesired charge state from the resultant mass spectrum may be varied smoothly, and is preferably increased as a function of ion drift time through the ion mobility separator. Alternatively, the minimum cut-off mass to charge ratio which is preferably applied to the obtained mass spectral data may be increased in a stepped manner as a function of ion drift time through the ion mobility separator.

Figure 5:
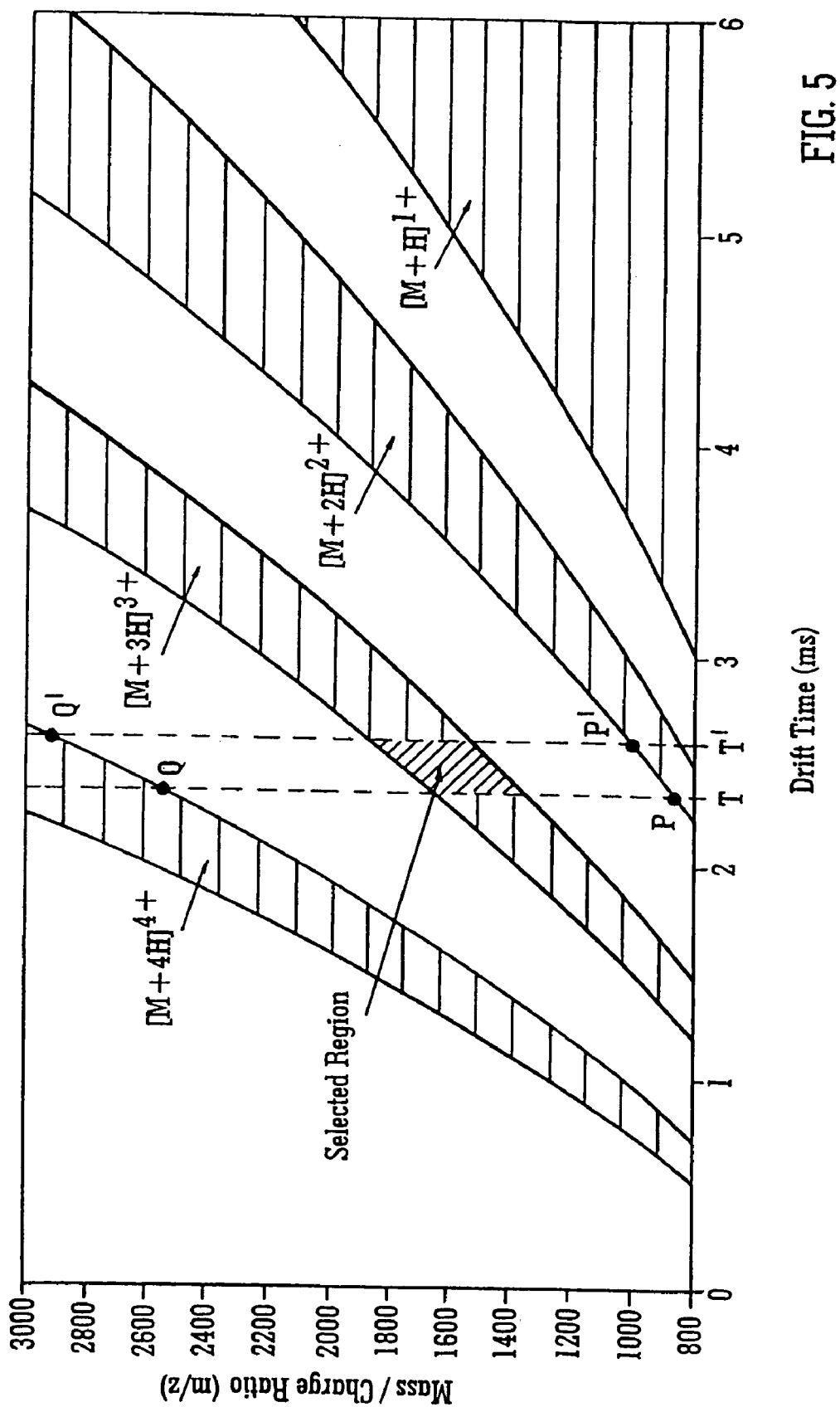
FIG. 5 illustrates the general principle of selecting mass spectral data relating to ions having a specific charge state according to an embodiment of the present invention.

FIG. 5 illustrates how the principle of forming a mass spectrum relating to doubly charged ions described in relation to FIG. 4 may be extended so that ions having a specific charge state(s) may be presented in the resultant mass spectrum and ions having other charge states being excluded. FIG. 5 shows how the mass spectral data may be post-processed so as to select ions of a specific charge state (in this case triply charged ions) in preference to ions having any other charge state. The mass spectral data obtained at a time T after ions have first been admitted or introduced into the ion mobility separator may be post-processed so as to select mass spectral data relating to ions having a mass to charge ratio >P and <Q, wherein P preferably lies on the upper threshold of the region containing doubly charged ions and Q preferably lies on the lower threshold of the region containing quadruply charged ions. Having processed the mass spectral data obtained at a time T the upper and lower mass to charge ratio cut-offs P, Q may then preferably increased so that for the mass spectral data obtained at a later time T', the lower mass to charge ratio cut-off applied to the mass spectral data has been increased from P to P' and the upper mass to charge ratio cut-off applied to the mass spectral data has been increased from Q to Q'. As with the embodiment described in relation to FIG. 4, the upper and lower mass to charge ratio cut-offs applied to the mass spectral data do not necessarily follow the lower and/or upper thresholds of any particular charge state region, and according to the other embodiments the upper and lower cut-offs applied to the mass spectral data may fall within one or more known intermediate regions and/or one or more of the bands in which ions having a particular charge state are known to be found. For example, in one embodiment, the lower and upper mass to charge ratio cut-offs applied to the mass spectral data may simply follow the thresholds of the region comprising doubly, triply, quadruply etc. charged ions. According to other embodiments mass spectral data relating to two, three, four or more charge states may be selected in preference to any other charge state (e.g. doubly and triply charged ions may be transmitted). Embodiments are also contemplated wherein non-neighbouring charge states (e.g. doubly and quadruply charged ions) are selected for presentation in the resulting mass spectrum but not ions having any other charge state.

Figure 6A:
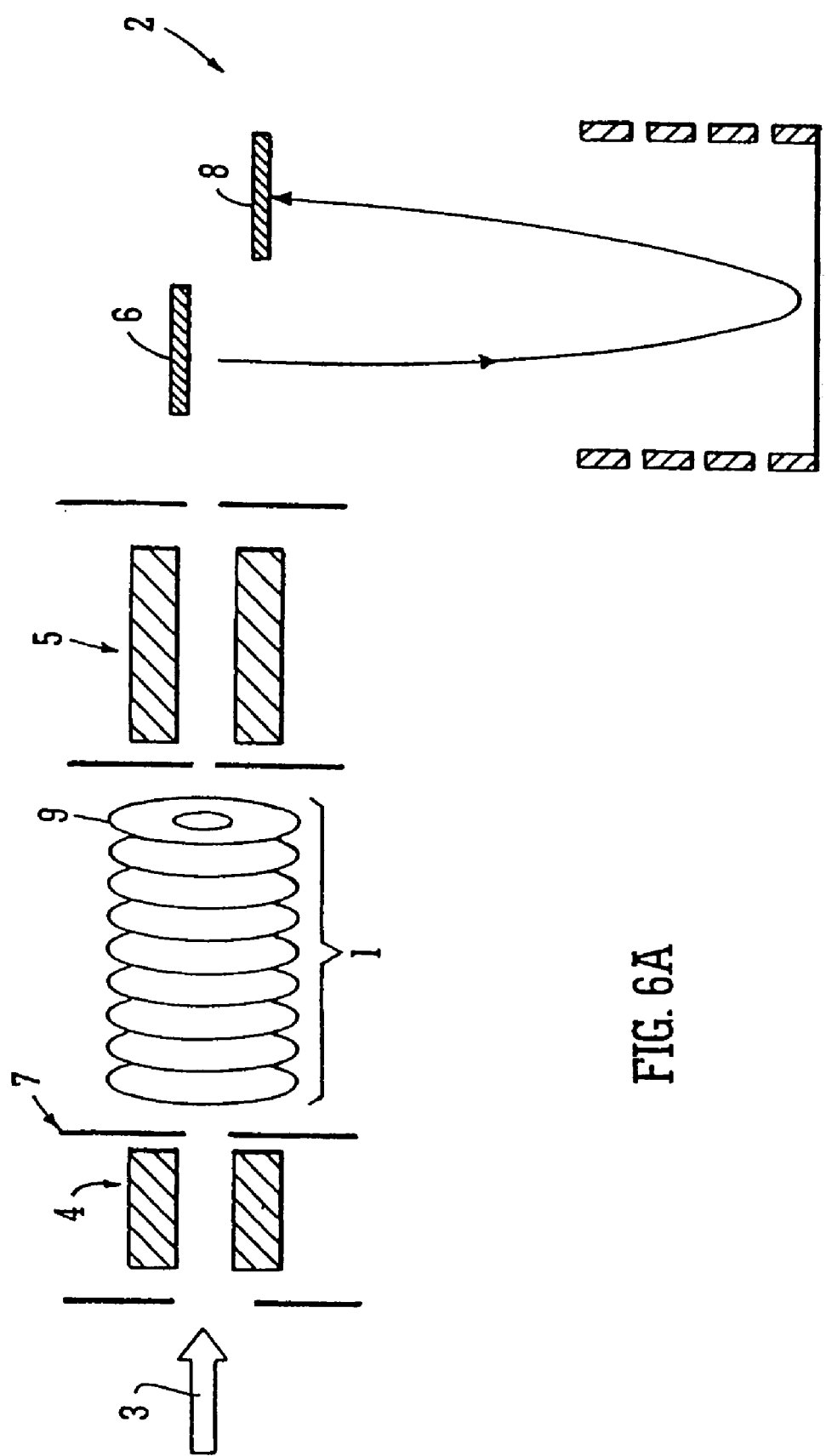
FIG. 6A shows a schematic of a basic embodiment of the present invention comprising an ion mobility separator upstream of an orthogonal acceleration Time of Flight mass analyser.
Figure 6B:
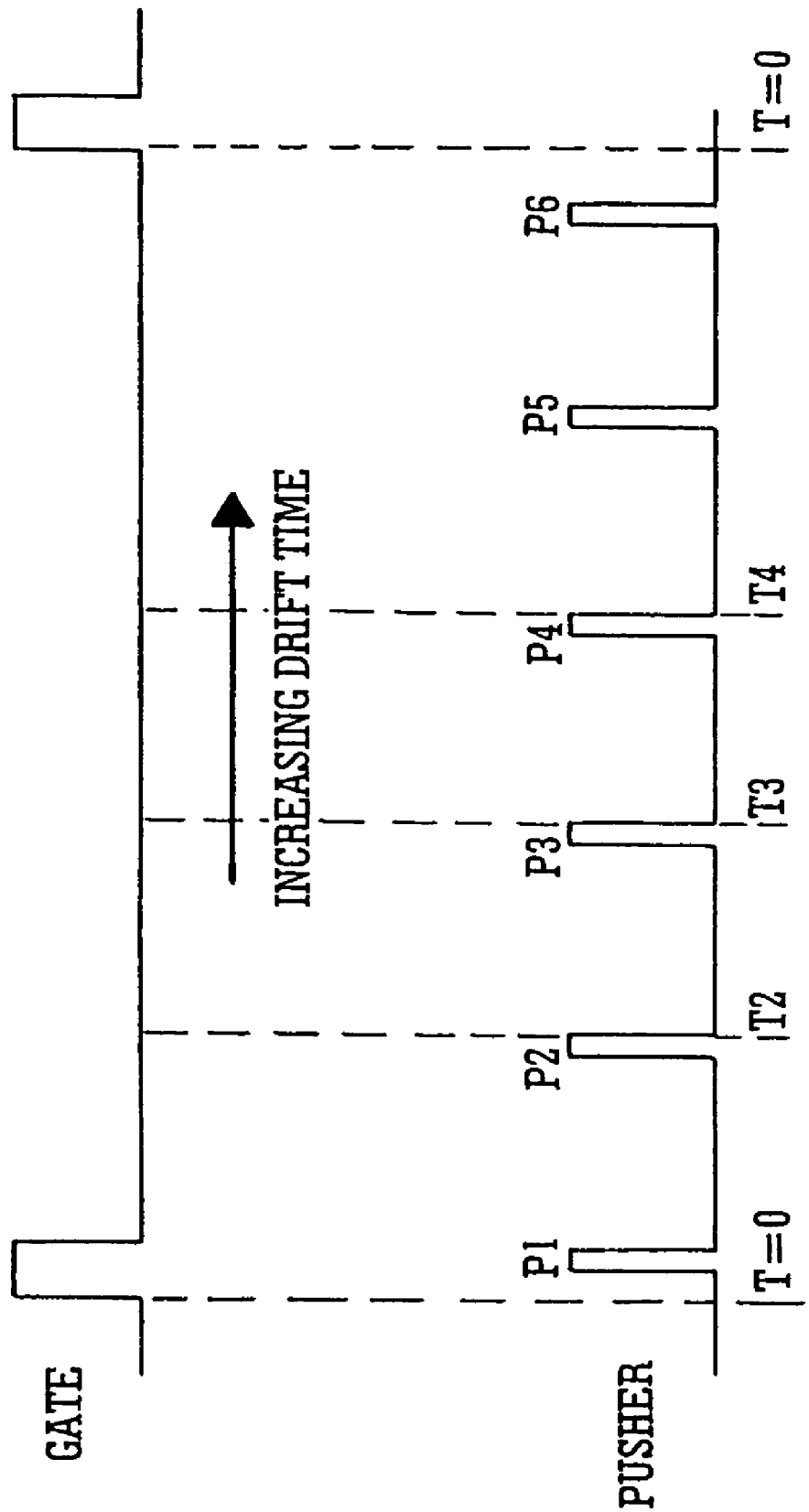
FIG. 6B illustrates how the pusher electrode of the Time of Flight mass analyser is preferably energised multiple times before a new pulse of ions is admitted to the ion mobility separator.

FIG. 6A shows a basic embodiment of the present invention. According to an embodiment a continuous ion source such as an Electrospray ion source generates a beam of ions 3. Ions are then preferably trapped in an ion trap 4 upstream of an ion mobility separator or spectrometer 1. The ions may then be pulsed out of the ion trap 4 by applying, for example, an extraction voltage to an ion gate 7 arranged at the exit of the ion trap 4 and upstream of the ion mobility separator 1. FIG. 6B illustrates the relationship between pulsing ions into the ion mobility separator 1 and subsequently mass analysing the ions. This will be described in more detail later.

The ion trap 4 may comprise a quadrupole rod set having, for example, a length of approximately 75 mm. However, according to another embodiment the ion trap 4 may comprise an ion tunnel ion trap comprising a plurality of electrodes having apertures therein. The apertures are preferably all the same size. In other embodiments at least 60%, 65%, 70%, 75%, 80%, 85%, 90% or 95% of the electrodes have apertures which are substantially the same size. The ion tunnel ion trap may preferably comprise approximately 50 electrodes. Adjacent electrodes of the ion trap 4 are preferably connected to opposite phases of an AC or RF voltage supply so that ions are radially confined in use within the ion trap 4.

The voltage applied to the ion gate 7 or other electrode which effectively traps ions in an ion trapping region upstream of the ion mobility separator 1 may be dropped for a short period of time thereby causing ions to be ejected from the ion trap 4 in a substantially pulsed manner into the ion mobility separator 1.

In less preferred embodiments, a pulsed ion source such as a Matrix Assisted Laser Desorption Ionisation ("MALDI") ion source or a Laser Desorption Ionisation ("LDI") ion source may be used instead of a continuous ion source. If a pulsed ion source is used, then ion trap 4 and ion gate 7 may be omitted.

The ion mobility separator 1 is a device which causes ions to become temporally separated as they pass through the ion mobility separator 1 according to their ion mobility. A number of different forms of ion mobility separator 1 may be used.

In one embodiment, the ion mobility separator 1 may comprise a drift tube (not shown) having a number of guard rings distributed within the drift tube. The guard rings may be interconnected by equivalent valued resistors and connected to a DC voltage source. A linear DC voltage gradient may be generated along the length of the drift tube. The guard rings are not connected to an AC or RF voltage source.

According to another more preferred embodiment the ion mobility separator 1 may comprise a number of ring, annular or plate electrodes, or more generally electrodes having an aperture therein through which ions are transmitted in use. The apertures are preferably all the same size and are preferably circular. In other embodiments at least 60%, 65%, 70%, 75%, 80%, 85%, 90% or 95% of the electrodes have apertures which are substantially the same size or area.

A schematic example of such an ion mobility separator 1 is shown in FIG. 7A. The ion mobility separator 1 may comprise a plurality of electrodes 1a, 1b which are either arranged in a single vacuum chamber, or as shown in FIG. 7A are arranged in two preferably adjacent vacuum chambers separated by a differential pumping aperture Ap1. In one embodiment, the portion of the ion mobility separator 1a in an upstream vacuum chamber may have a length of, for example, approximately 100 mm, and the portion of the ion mobility separator 1b in a downstream vacuum chamber may have a length of, for example, approximately 85 mm. The ion trap 4, ion gate 7 and upstream portion 1a of the ion mobility separator 1 may be provided in the same vacuum chamber which is preferably maintained, in use, at a pressure within the range 0.1–10 mbar. According to less preferred embodiments, the vacuum chamber housing the upstream portion 1a may be maintained at a pressure greater than 10 mbar up to a pressure at or near atmospheric pressure. Also, according to less preferred embodiments, the vacuum chamber may alternatively be maintained at a pressure below 0.1 mbar.

The electrodes comprising the ion trap 4 may be maintained at a DC voltage $V_{rf1}$. Ion gate 7 may be normally held at a higher DC voltage $V_{trap}$ than $V_{rf1}$, but the voltage applied to the ion gate 7 may be periodically dropped to a voltage $V_{extract}$ which is preferably lower than $V_{rf1}$ thereby causing ions to be accelerated out of the ion trap 4 and to be admitted into the ion mobility separator 1.

Adjacent electrodes which form part of the ion trap 4 are preferably connected to opposite phases of a first AC or RF voltage supply in order to radially confine ions within the ion trap 4. The first AC or RF voltage supply preferably has a frequency within the range 0.1–3.0 MHz, preferably 0.5–1.1 MHz, further preferably 780 kHz.

Alternate electrodes forming the upstream section 1a of the ion mobility separator 1 are preferably capacitively coupled to opposite phases of the first AC or RF voltage supply.

The electrodes comprising the ion trap 4, the electrodes comprising the upstream portion 1a of the ion mobility separator 1 and the differential pumping aperture Ap1 separating the upstream portion 1a from the downstream portion 1b of the ion mobility separator 1 are preferably interconnected via resistors to a DC voltage supply which in one embodiment comprises a 400 V supply. The resistors interconnecting electrodes forming the upstream portion 1a of the ion mobility separator 1 may be substantially equal in value in which case an axial DC voltage gradient is obtained as shown in FIG. 7B. The DC voltage gradient is shown, for ease of illustration only, as being linear but in practice the DC voltage gradient may at least partially be stepped. An applied AC or RF voltage is superimposed upon the DC voltage and serves to radially confine ions within the ion mobility separator 1. The DC voltage $V_{trap}$ or $V_{extract}$ applied to the ion gate 7 preferably floats on the DC voltage supply. The first AC or RF voltage supply is preferably isolated from the DC voltage supply by a capacitor.

In a similar manner, alternate electrodes forming the downstream portion 1b of the ion mobility separator 1 are preferably capacitively coupled to opposite phases of a second AC or RF voltage supply. The second AC or RF voltage supply preferably has a frequency in the range 0.1–3.0 MHz, preferably 1.8–2.4 MHz, further preferably 2.1 MHz. In a similar manner to the upstream portion 1a, a substantially linear or stepped axial DC voltage gradient is maintained along the length of the downstream portion 1b of the ion mobility separator 1. As with the upstream portion 1a the applied AC or RF voltage is superimposed upon the DC voltage and serves to radially confine ions within the ion mobility separator 1. The DC voltage gradient maintained across the upstream portion 1a is preferably not the same as the DC voltage gradient maintained across the downstream portion 1b. According to a preferred embodiment, the DC voltage gradient maintained across the upstream portion 1a is greater than the DC voltage gradient maintained across the downstream portion 1b.

The pressure in the vacuum chamber housing the downstream portion 1b is preferably in the range $10^{-3}$ to $10^{-2}$ mbar. According to less preferred embodiments, the pressure may be above $10^{-2}$ mbar, and could be similar in pressure to the pressure of the vacuum chamber housing the upstream portion 1a. It is believed that the greatest temporal separation of ions occurs in the upstream portion 1a due to the higher background gas pressure. If the pressure is too low then the ions will not make enough collisions with gas molecules for a noticeable temporal separation of the ions to occur.

The size of the orifice in the ion gate 7 is preferably of a similar size or is substantially the same internal diameter or size as the differential pumping aperture Ap1. Downstream of the ion mobility separator 1 another differential pumping aperture Ap2 may be provided. The apertures of the electrodes forming the ion mobility separator 1 are preferably all the same size. In other embodiments at least 60%, 65%, 70%, 75%, 80%, 85%, 90% or 95% of the electrodes have apertures which are substantially the same size.

In another embodiment the ion mobility separator 1 may comprise an ion tunnel comprised of a plurality of segments. In one embodiment 15 segments may be provided. Each segment may comprise two electrodes having apertures interleaved with two other electrodes also having apertures. All four electrodes in a segment may be maintained at substantially the same DC voltage but adjacent electrodes are preferably connected to opposite phases of the same AC or RF supply. The DC and AC/RF voltage supplies are isolated from one another. Preferably, at least 90% of all the electrodes forming the ion mobility separator 1 comprised of multiple segments have apertures which are substantially similar or the same in size.

Typical drift times through the ion mobility separator 1 may be of the order of a few ms. After all the generated ions have traversed the ion mobility separator 1 a new pulse of ions may be admitted to the ion mobility separator which marks the start of a new cycle of operation. Many cycles (e.g. 200 or more) may be performed in a single experimental run (which may last, for example, 1s).

A collision or gas cell and/or quadrupole mass filter (not shown in FIG. 6A) may be provided preferably downstream of the ion mobility separator 1 and upstream of the transfer lens 5. Ions may be arranged so that they are sufficiently energetic when they enter the collision cell so that they collide with gas molecules present in the gas cell and fragment into daughter ions. Subsequent mass analysis of the daughter ions yields valuable mass spectral information about the parent ion(s). Ions may also be arranged so that they enter the gas or collision cell in another mode of operation with much less energy, in which case they may not substantially fragment. The energy of ions entering the collision cell can be controlled e.g. by setting the level of a voltage gradient experienced by the ions prior to entering the collision cell. Since the voltage gradient can be switched near instantaneously, the collision cell can, in effect, be considered to be switchable between a relatively high fragmentation mode and a relatively low fragmentation mode.

A transfer lens 5 may be provided downstream of the ion mobility separator 1 to guide ions through a further differential pumping aperture and into an analyser chamber containing a Time of Flight mass analyser. The mass analyser is preferably an orthogonal acceleration Time of Flight mass analyser 2 having a pusher and/or puller electrode 6 for injecting ions into an orthogonal flight region. A reflectron is preferably provided for reflecting ions travelling through the orthogonal flight region back towards an ion detector 8. As is well known in the art, at least some of the ions in a packet of ions entering an orthogonal acceleration Time of Flight mass analyser will be orthogonally accelerated into the orthogonal flight region. Ions will become temporally separated in the orthogonal flight region in a manner dependent upon their mass to charge ratio. Ions having a lower mass to charge ratio will travel faster in the flight region and will reach the ion detector 8 prior to ions having a higher mass to charge ratio. The time it takes for an ion to travel through the flight region and to reach the ion detector 8 can be used to accurately determine the mass to charge ratio of the ion in question. The intensity of the detected ions and their mass to charge ratios can be used to produce a mass spectrum.

According to a less preferred embodiment the Time of Flight mass analyser may comprise an axial Time of Flight mass analyser. Ions may be pulsed into the axial Time of Flight region. In order to pulse ions into an axial flight region, a second ion trap and optionally a second ion gate may be provided upstream of the axial flight region. Ions received from the ion mobility separator 1 may be trapped in the second ion trap. Packets of ions may then preferably be periodically released from the second ion trap, for example, by lowering the DC voltage applied to the second ion gate in a similar manner to the way ions may be released from the first ion gate 7 into the ion mobility separator 1. In other embodiments, however, the second ion trap may trap and release ions without requiring a distinct second ion gate to be provided.

The second ion trap may comprise an ion tunnel ion trap comprising a plurality of electrodes having apertures therein. The electrodes may take the form of rings or other annular shape or rectangular plates. Preferably at least 60%, 65%, 70%, 80%, 85%, 90% or 95% of the electrodes forming the second ion trap have apertures which are substantially the same size or area. Adjacent electrodes are preferably connected to opposite phases of an AC or RF voltage supply so that ions are radially confined within the second ion trap. A particular advantage of an ion tunnel ion trap is that the DC voltage supplied to each electrode can be individually controlled. This enables numerous different axial DC voltage profiles to be created along the length of the ion tunnel ion trap. A particularly preferred embodiment is to provide, in one mode of operation, a V-shaped DC potential profile comprising an upstream portion having a negative DC voltage gradient and a downstream portion having a positive DC voltage gradient so that (positive) ions become trapped towards the centre of the ion trap. If the positive DC voltage gradient maintained across the downstream portion of the ion trap is then changed to a zero gradient or more preferably to a negative gradient, then (positively charged) ions will be accelerated out the ion trap as a pulse of ions. In this particular embodiment a distinct second ion gate may then become redundant.

According to other embodiments, the second ion trap may comprise a 3D-quadrupole ion trap comprising a central doughnut shaped electrode together with two endcap electrodes. According to another embodiment, the second ion trap may comprise a hexapole ion guide. However, this embodiment is less preferred since no axial DC voltage gradient is present to urge ions out of the hexapole ion guide. It is for this reason that an ion tunnel ion trap is particularly preferred.

The second ion trap may also act both as an ion trap and as a collision cell. The ion tunnel ion trap/collision cell may comprise a plurality of segments (e.g. 15 segments), each segment comprising four electrodes interleaved with another four electrodes. All eight electrodes in a segment may be maintained at the same DC voltage, but adjacent electrodes are preferably supplied with opposite phases of an AC or RF voltage supply. A collision gas preferably nitrogen or argon may be supplied to the collision cell at a pressure preferably in the range $10^{-3}$–$10^{-2}$ mbar. Ions may be trapped and/or fragmented in the ion trap/collision cell by appropriate setting of the DC voltages applied to the electrodes and the energy that ions are arranged to have upon entering the ion trap/collision cell.

According to a preferred embodiment both the upstream ion trap 4 and the ion mobility separator 1 may comprise an ion tunnel i.e. a plurality of electrodes wherein each electrode has an aperture therein through which ions are transmitted in use. The electrodes forming the ion trap 4 and/or ion mobility separator 1 preferably have substantially similar sized apertures and may comprise a substantially square or rectangular plate electrode or a ring or circular electrode. The apertures are preferably circular. According to various embodiments, the ion trap 4 and/or ion mobility separator 1 may comprise at least 10, 20, 30, 40, 50, 60, 70, 80, 90 or 100 electrodes of which at least 60%, 65%, 70%, 75%, 80%, 85%, 90% or 95% may have apertures which are substantially the same size or area.

Embodiments of the invention are also contemplated wherein the DC voltage profile along the length of the ion mobility separator 1 and/or ion trap 4 and/or collision cell is not strictly linear, but rather has a stepped profile.

Ions 3 from, for example, an Electrospray ion source are preferably stored in the ion trap 4 or other ion trapping device and are then subsequently pulsed periodically into the ion mobility separator 1. As can be seen from FIG. 38 the typical drift time of ions through an ion mobility separator will be the order of a few ms. During this period the orthogonal acceleration electrode 6 of the Time of Flight mass analyser 2 is energised multiple times. For example, ions pulsed into the ion mobility separator 1 may take up to 10 ms to drift through the ion mobility separator 1. Ions emerging from the ion mobility separator 1 are onwardly transmitted to the pusher electrode 6 of the Time of Flight mass analyser 2 which may be energised with a repetition rate of, for example, 50 μs. According to other embodiments the repetition rate may be <10 μs, 10–20 μs, 20–30 μs, 30–40 μs, 40–50 μs, 50–60 μs, 70–80 μs, 80–90 μs, 90–100 μs or >100 μs. Accordingly, the pusher electrode 6 may be energised, for example, 200 per pulse of ions into the ion mobility separator 1. The mass spectral data from the 200 or so mass analyses may then be post-processed and a composite mass spectrum may then be generated from the processed mass spectral data. After all the ions have been transmitted through the ion mobility separator 1 a new pulse of ions may be released from the ion trap 4 into the ion mobility separator 4 and the process may start again. For example, during a 1 s period ions may be pulsed 100 times into the ion mobility separator 1 with 200 sets of mass spectral data being obtained per pulse of ions into the ion mobility separator 1. Accordingly, during a 1 s experimental run 20,000 sets of mass spectral data may be obtained.

The time taken for an ion to travel through the ion mobility separator 1, to emerge there from and then to arrive at the pusher electrode 6 of the Time of Flight mass spectrometer 2 will depend upon the mobility of the ion. Ions having a higher mobility will take a shorter time to travel through the ion mobility separator 1 compared with ions having a relatively lower ion mobility.

FIG. 6B illustrates the time relationship between ions being pulsed into the ion mobility separator 1 and the energisation of the pusher electrode 6. For ease of illustration only six pusher pulses are shown per gate pulse. However, as has already been discussed above the pusher electrode may more typically be energised for example 100–200 times per pulse of ions into the ion mobility separator 1. The ions arriving at the ion detector 8 of the Time of Flight mass analyser 2 from pusher pulse P1 will have a higher mobility than the ions arriving at the ion detector 8 from subsequent pusher pulse P2 etc. The ions arriving at the ion detector 8 from pusher pulse Pn will therefore have a higher mobility than the ions arriving at the ion detector 8 from pusher pulse Pn+1. Ions arriving at the ion detector 8 from a pusher pulse Pn will produce a set of mass spectral data which corresponds with ions having a specific ion mobility associated with pusher pulse Pn. Summing all the mass spectra data from all the pusher pulses which occur during a single gate pulse period (i.e. the time between subsequent pulses of ions into the ion mobility separator 1) in a conventional manner will give an integrated or composite mass spectrum comprising all ions irrespective of their mass charge ratio ion mobility and therefore hence charge state.

The mass spectral data acquired due to a particular pusher pulse Pn can be considered as a vertical section through the plot of FIG. 3B at a particular drift time Tn, where Tn is defined as the time delay from the gate pulse (i.e. release of ions into the ion mobility separator 1) to the pusher pulse Pn (i.e. energisation of electrode 6).

According to a less preferred embodiment the Time of Flight mass analyser acquisition for a particular pusher push Pn may be configured to only acquire, store or otherwise record mass spectral data relating to ions arriving after a particular cut-off flight time. For example, this cut-off flight time may lie between the doubly charged and singly charged bands shown in FIG. 3B. Therefore, the resultant mass spectrum would then contain only doubly (or higher order) charged ions. In effect, the mass spectral data would be processed on the fly or only recorded in the first place in accordance with a pre-determined manner. Such an approach would reduce the amount of mass spectral data to be processed but is less flexible than the preferred embodiment which acquires full sets of data and then post-processes the data.

Figure 8:
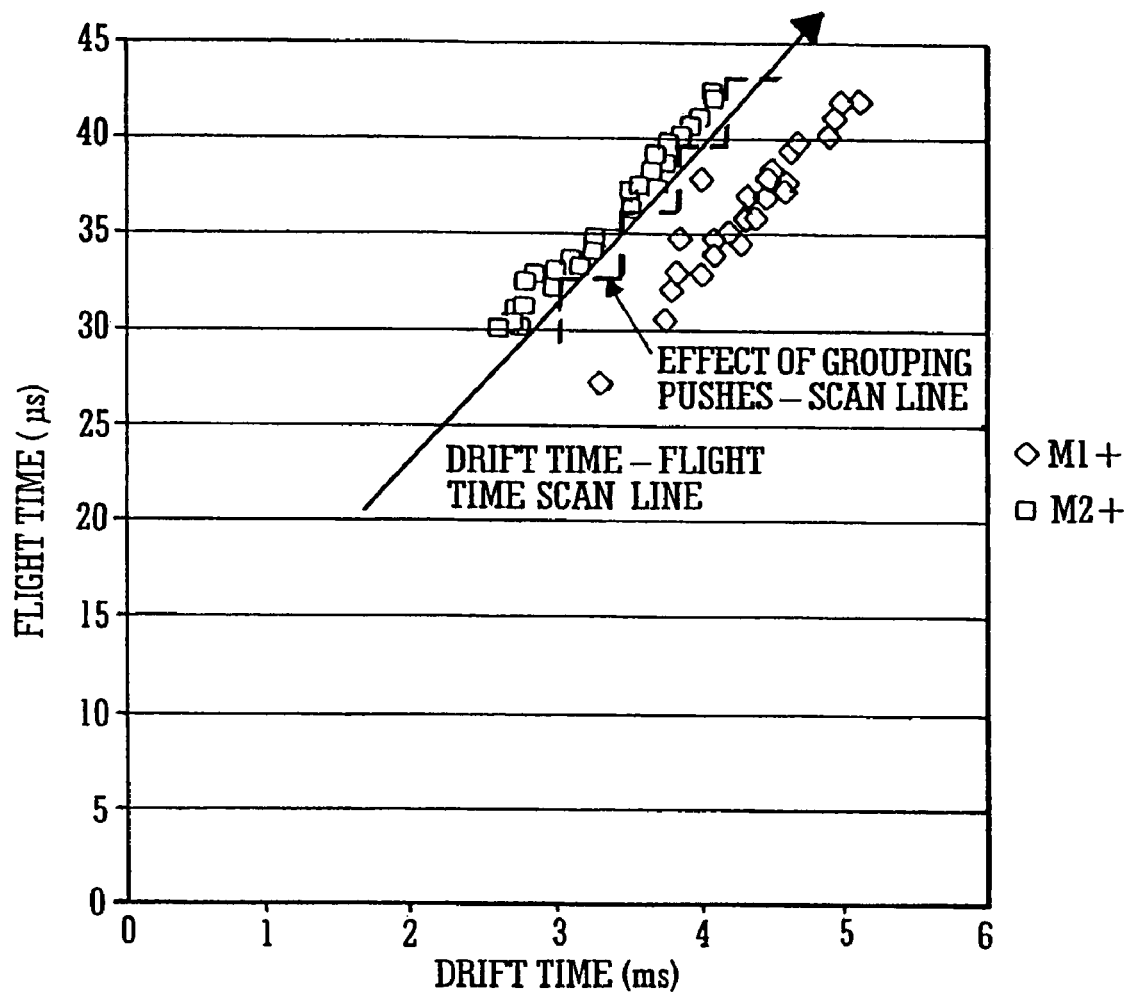
FIG. 8 illustrates how mass spectral data may be processed so that ions having a desired charge state(s) may be used to provide a composite mass spectrum which effectively excludes ions having an undesired charge state.

The desired value for the cut-off flight time which is preferably applied to the mass spectral data or less preferably to the initial recording of data may vary from pusher pulse Pn to pusher pulse Pn+1 and may, for example, follow the solid arrow shown in FIG. 8. If the flight time cut-off did follow the solid arrow shown in FIG. 8 then the summation of all the mass spectra from all the pusher pulses in a single gate period would then give a resultant integrated spectrum which comprised multiply charged ions only i.e. singly charged ions would have been effectively filtered out.

It will be appreciated that the characteristic band of ion drift times through the ion mobility separator 1 versus ion flight time through the flight region of the Time of Flight mass analyser for triply charged ions lies to the left of the characteristic band for doubly charged ions shown in FIG. 8 as has already been discussed in relation to FIG. 5. The characteristic band of the ion drift time of an ion versus the flight time of the ion for charge state (n+1) similarly lies at lower drift times than the characteristic band for charge state n. By using combinations of ion mobility dependent low time of flight and high time of flight cut-offs which vary, preferably increase with drift time, it is possible to select ions having a particular charge state or combination of charge states. An upper flight time cut-off used in conjunction with a lower flight time cut-off allows a band-pass mode of filtering the mass spectral data and specific charge states to be selected. It is possible to define multiple band-passes and therefore to select any desired combination of charge states.

According to the preferred embodiment all the ions injected into the Time of Flight mass analyser 2 for a given push Pn are subsequently detected and recorded. However, software is then preferably used to the selectively disregard ions having flight times below a minimum flight time as indicated by the scan line shown in FIG. 8 for a particular push event Pn. Summation of the processed mass spectral data results in an integrated or composite mass spectrum containing only doubly (or higher order) charged ions. This software approach also allows multiple band-passes to be generated as previously mentioned, allowing any combination of charge states to be selected.

According to another embodiment mass spectral data relating to multiple pushes may be grouped together and a time of flight cut-off for the group of pushes defined Accordingly, the cut-off flight time applied to the mass spectral data would increase in steps (for example like the dashed line in FIG. 8). This approach would also lead to an improvement in filtering out undesired charge states from the final mass.

Figure 9:
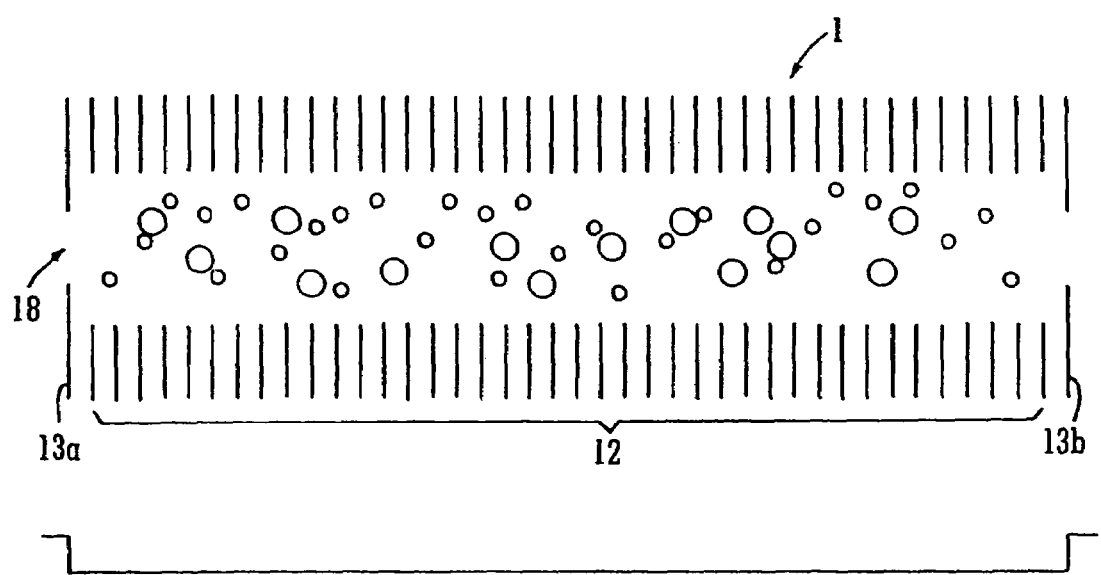
FIG. 9 shows an ion mobility separator according to another embodiment in an initial state of equilibrium prior to one or more transient DC voltages being applied to the electrodes forming the ion mobility separator.

FIG. 9 shows another preferred form of ion mobility separator 1 which comprises a plurality of electrodes 12 each having an aperture through which ions are transmitted in use. Adjacent electrodes 12 are preferably connected to opposite phases of an AC or RF voltage supply. The ion mobility separator 1 is preferably held at a pressure such that ions traversing its length undergo many collisions with gas molecules. The ion mobility separator 1 may according to one embodiment receive ions generated by an Electrospray or a MALDI ion source. One or more end plates or electrodes 13a, 13b of the ion mobility separator 1 may be maintained at a slight positive voltage relative to the other electrodes 12 so that ions once entering the ion mobility separator 1 are effectively trapped within the ion mobility separator 1 and are therefore unable to surmount the potential barrier at one or both ends. After a certain period of time equilibrium may be reached within the ion mobility separator 1 so that ions of all masses and mobilities are substantially equally distributed along the length of the ion mobility separator 1 as shown in FIG. 9.

Figure 10:
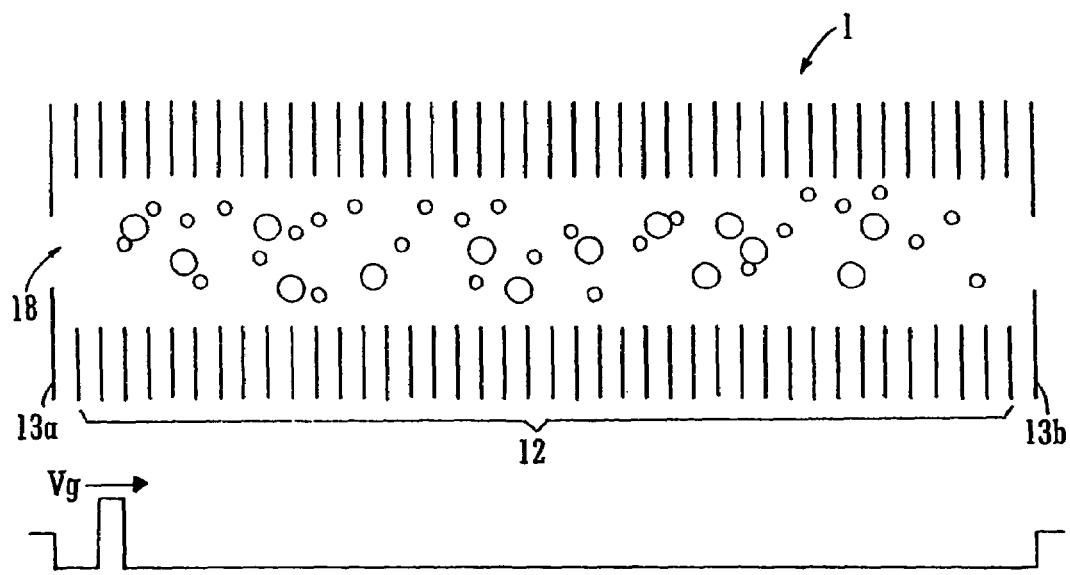
FIG. 10 shows a transient DC voltage pulse being generated at one end of the ion mobility separator.

As shown in FIG. 10, according to one embodiment a voltage pulse Vg may be applied to an electrode adjacent to one of the end plates 13a so that some ions will be pushed by the applied voltage pulse Vg along the ion mobility separator 1. The local field variation is given by:

$$V_{drift} = KE(x)$$

where $V_{drift}$ is the drift velocity of an ion, K is the mobility of the ion and E(x) is the electric field caused by the applied voltage. The electric field resulting from the applied voltage decays rapidly to a negligible value within a few electrode spacings.

The voltage pulse Vg is then preferably rapidly switched to the next adjacent electrode. An ion which has had enough time to drift at least one electrode spacing along the ion mobility separator 1 will therefore experience the same force and will again move along the ion mobility separator 1 in the direction in which the voltage pulse Vg is heading. However, ions having a lower ion mobility may not have had sufficient time to drift far enough to see the influence of the voltage when it is switched to the adjacent electrode. Accordingly, these lower mobility ions will be effectively left behind by the travelling voltage pulse Vg or voltage waveform.

Figure 11:
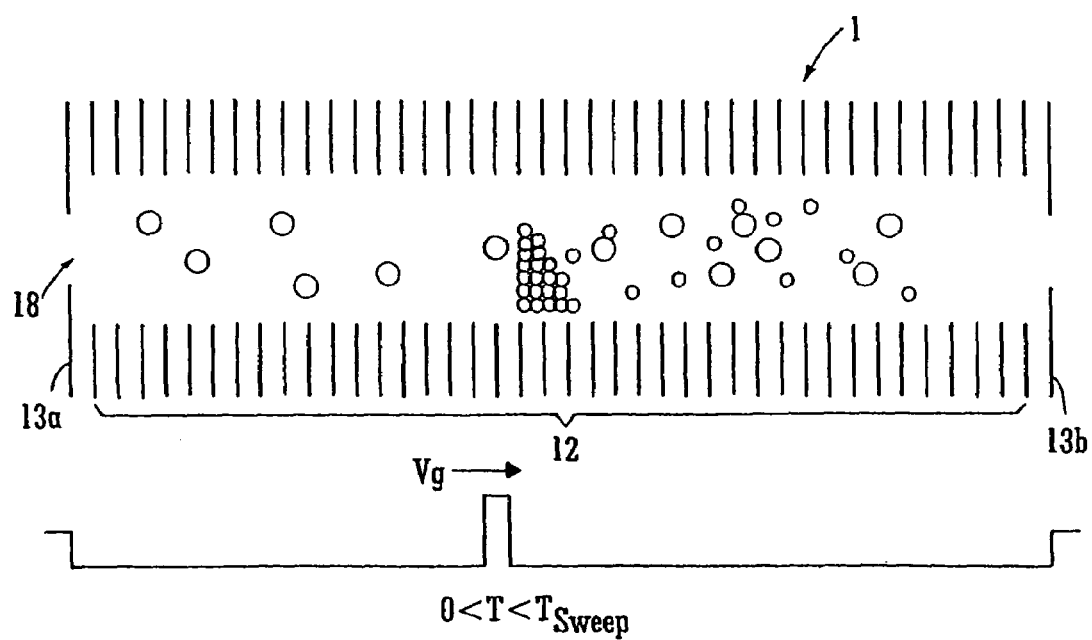
FIG. 11 shows the transient DC voltage pulse sweeping relatively high mobility ions with it towards an exit of the ion mobility separator.
Figure 12:
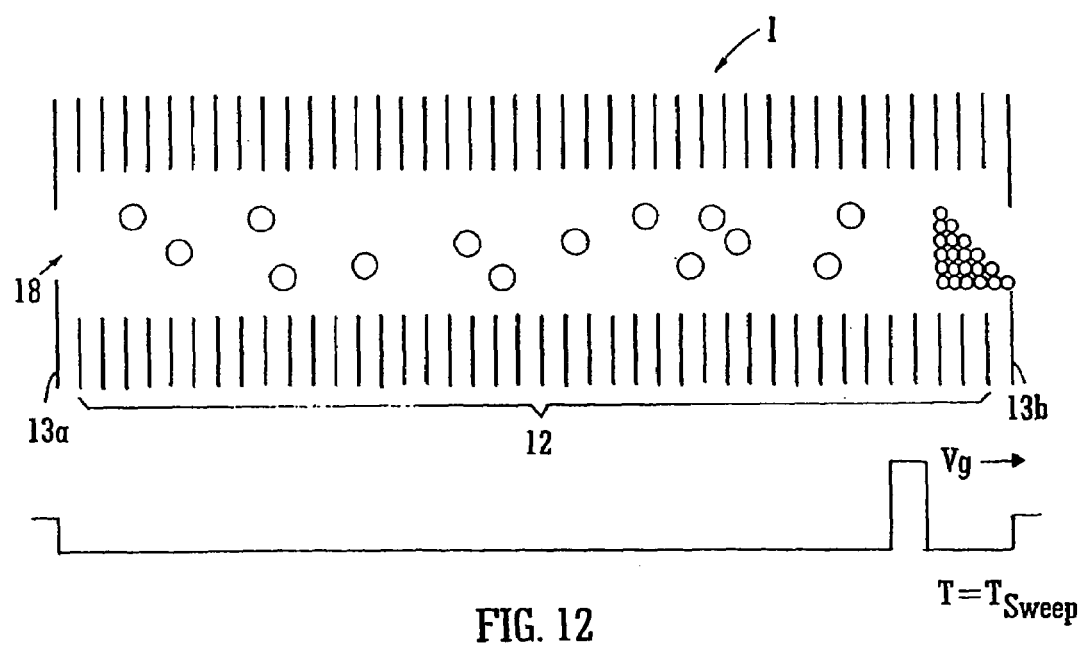
FIG. 12 shows relatively high mobility ions immediately prior to being ejected from the ion mobility separator.

The voltage pulse Vg preferably travels along the ion mobility separator 1 from electrode to electrode sweeping those ions with a sufficiently high ion mobility with it. As shown in FIGS. 11 and 12 the ion mobility separator 1 may therefore, in one embodiment, act as a high pass ion mobility filter such that ions having ion mobilities greater than a certain value are preferably ejected from the ion mobility separator 1 whereas ions having lower ion mobilities remain substantially trapped within the ion mobility separator 1. FIG. 12 shows ions at the end of a voltage sweep being ejected from the ion mobility separator 1.

The sweep time $T_{sweep}$ of the ion mobility separator 1 may then be reduced to select a slightly lower (intermediate) ion mobility so that those ions having an intermediate ion mobility may then be subsequently ejected from the ion mobility separator 1. By gradually further reducing the sweep time a complete mobility scan may be built up until the ion mobility separator 1 is substantially empty of ions.

According to another mode of operation the amplitude of the voltage pulse Vg may be progressively increased with each sweep thereby collecting ions having progressively decreasing ion mobilities in the same way. It will be appreciated from consideration of the above equation that doubling the voltage will double the velocity of an ion.

The resolution of the ion mobility separator 1 will in part be determined by the sweep time $T_{sweep}$ or voltage increment. The smaller the step (i.e. reduction in sweep time or increase in the amplitude of the voltage pulse) between the adjacent sweeps the greater the resolution of the ion mobility separator 1.

Figure 13:
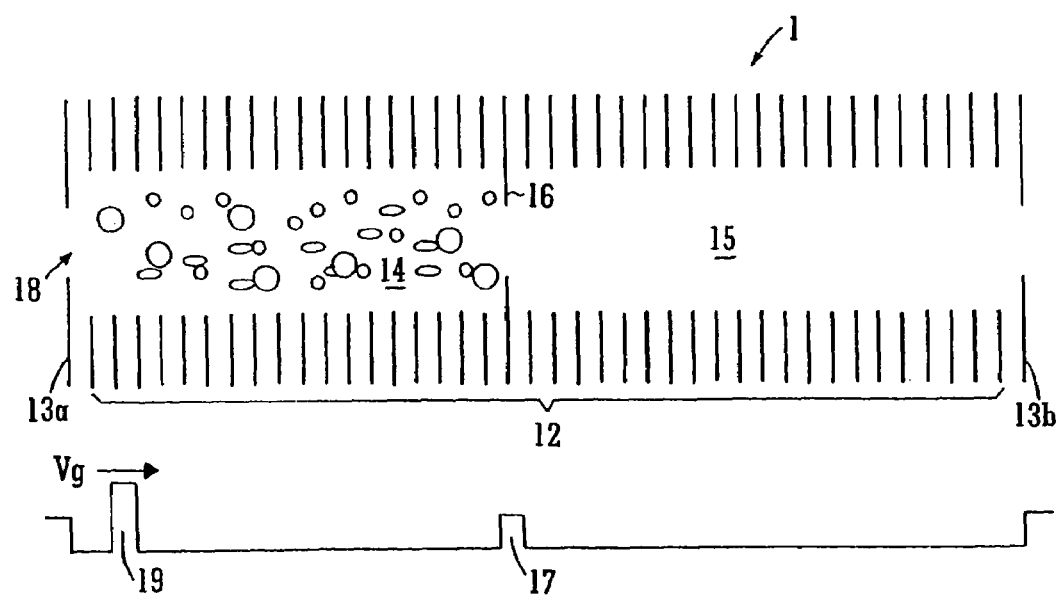
FIG. 13 illustrates the initial stage of a bandpass mode of ion mobility separation.
Figure 14:
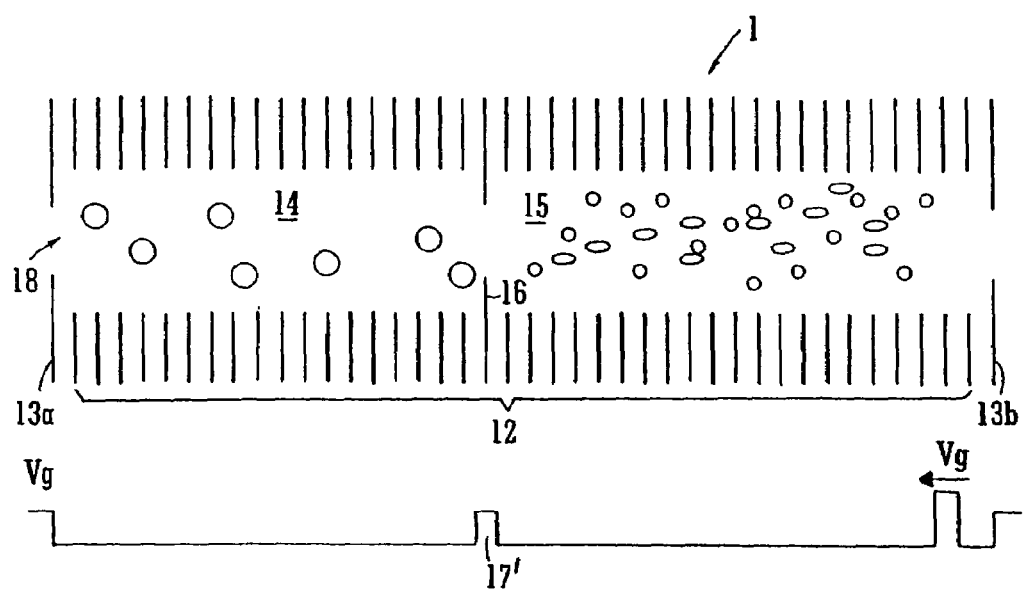
FIG. 14 shows ions having relatively high and intermediate ion mobilities having been swept into a separate region of the ion mobility separator and hence been effectively isolated from relatively low mobility ions.
Figure 15:
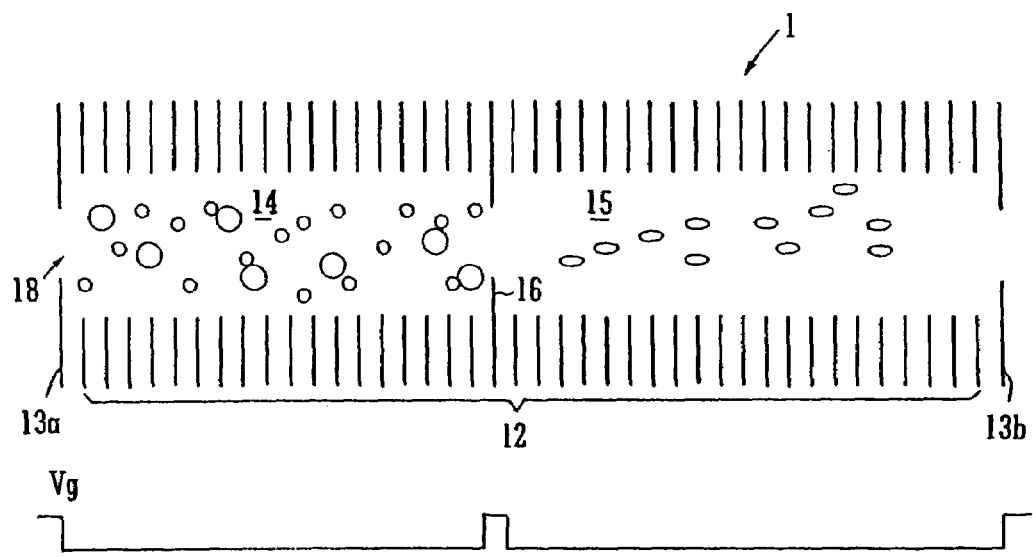
FIG. 15 illustrates how ions having a relatively high ion mobility may be swept out of the separate region thereby leaving ions having an intermediate ion mobility in the separate region.

The mode of operation described above may build up a mobility spectrum by a series of high pass further steps. However, isolation of a particular range of ion mobilities i.e. bandpass operation may also be achieved by employing a two stage device. As shown in FIG. 13, ions with an ion mobility greater than a certain value may be arranged to pass along a portion of the ion mobility separator 1 by the operation of a voltage pulse Vg passing along the ion mobility separator 1. The ions from a first region 14 move towards an electrode 16 which is maintained at a certain potential 17 such that ions having a minimum ion mobility which pass through the electrode 16 into a second region 15 which is preferably substantially empty of ions. As shown in FIG. 14, once some ions have been swept into the second region 15 the travelling voltage pulse Vg may then be reversed so as to sweep some ions from the second region 15 past the same (or another electrode) which is preferably maintained at a lower potential 17' back into the first region 14. The reverse sweep may be faster and/or have a higher voltage than the forward sweep so that as shown in FIG. 15 ions having ion mobilities within a desired intermediate range may remain trapped in the second region 15 whereas higher and lower mobility ions are located in the first region 14.

The resolution of the ion nobility separator 1 has been modelled to include the effect of diffusion of ions. Diffusion effects are known to degrade the resolution of drift tube ion mobility separators and the relationship between the drift tube length and the applied axial voltage drop is given by:

$$\frac{|X|}{L} = \frac{0.173}{\sqrt{V}}$$

where mod X is the spatial spread due to diffusion, L is the length of the drift tube and V the applied axial voltage drop.

To increase the resolving power of a drift tube mobility spectrometer longer drift tubes and higher voltages may be employed. However, an advantage of the preferred ion mobility separator 1 is that the voltage required can be a relatively low e.g. 10V at a pressure of 2 mbar. Furthermore, the low (10V) voltage only needs to be applied to a single electrode at any one point in time. The preferred ion mobility separator 1 can therefore achieve ion mobility separation using a low voltage source whereas a conventional drift tube type ion mobility separator would require approximately 1000V to achieve comparable ion mobility separation.

Further improvements in resolution may be achieved by sweeping the ions backwards and forwards through the same volume a number of times. This has the effect of increasing the effective length of the ion mobility separator 1 without actually increasing its physical dimensions. A compact ion mobility separator is therefore provided. As will be appreciated, a greater number of passes through the ion mobility separator 1 allows for greater isolation of the desired species of ions.

Ions may be purged from the swept volume after the passage of the travelling voltage wave by switching the AC or RF voltage applied to the electrodes 12 OFF and allowing ions to diffuse out of that portion of the ion mobility separator 1. After a desired number of passes of the same volume the ions may be allowed out of the ion mobility separator 1 for subsequent mass analysis.

The ion mobility separator 1 according to the preferred embodiment can advantageously operate at duty cycles approaching 100% as it can be arranged to eject only ions having a desired ion mobility whilst storing the other ions for further analysis. This is in contrast to a Field Asymmetric Ion mobility separator (FAIMS) which is a scanning device whereby ions that are not transmitted are lost to the walls of the device.

An embodiment is contemplated wherein a quadrupole mass filter is provided downstream of a preferred ion mobility separator 1 and set to a discrete mass to charge ratio transmission window so as to match the desired mobility range ejected by the preferred ion mobility separator 1. This means that the desired ions are stable in the quadrupole mass filter all through the device. The equivalent to a scanning experiment can therefore be performed in a stepped manner with no loss in duty cycle as unejected ions are still stored by the ion mobility separator 1.

In addition to embodiments wherein a single transient DC potential or pulse Vg is translated along the length of the ion mobility separator 1, according to other embodiments a travelling DC voltage wave having a repeating waveform may be used to separate ions according to their ion mobilities. The amplitude and velocity of the one or more DC voltage waveforms may be arranged such that ions do not surf on a single voltage pulse along the drift region but instead roll over the top of subsequent pulses thereby receiving a succession of nudges leading to an overall drift in the wave direction. The transit time of an ion through the ion mobility separator 1 will therefore be dependent upon its ion mobility.

According to this embodiment a travelling wave ion guide may be used to provide the drift region. The ion guide may comprise either a stack of plates or a segmented multipole rod set. An ion trapping region upstream of the drift region may be provided with an ion gate to periodically pulse bunches of ions from the ion trap into the drift region.

The travelling DC voltage wave form may comprise periodic pulses of constant amplitude and velocity. A reverse DC gradient may be superimposed on the travelling DC voltage waveform so that the field acts between pulses to move ions back towards the upstream ion gate or the entrance of the ion mobility separator 1. Such a DC voltage waveform may enhance the separation characteristics of the ion mobility separator 1 and may be used to prevent ions having an ion mobility less than a certain value from travelling with the travelling DC voltage wave and exiting the ion mobility separator 1.

According to another embodiment the DC potential waveform may be such that the height of the voltage pulses reduces along the drift region as the potential due to an axial DC voltage gradient increases. Such a waveform may also enhance separation. Furthermore, the DC voltage waveform may be such that ions having a certain ion mobility may find balance points along the length of the drift region where the movement caused by the travelling DC voltage wave is counteracted by the reverse axial DC voltage gradient. Ions of different mobility may therefore find different balance points along the length of the ion mobility separator 1. A static mobility separation may therefore be produced and ions of similar mobility may collect in specific regions. These ions may be transmitted in a band-pass operation. The mode of operation using such a voltage waveform does not necessarily require an ion gate since it may operate with a continuous ion beam. Furthermore, the DC axial field may be constant or variable with position. This may be achieved by applying potentials to the electrodes forming the ion guide which increase linearly or non-linearly. Alternatively, the amplitude of the travelling DC voltage wave may decrease linearly or non-linearly as it progresses from the entrance to the exit of the ion mobility separator 1. The DC axial field and amplitude of the travelling wave may change with position. In one particular embodiment the DC axial field may continuously increase from the entrance to the exit of the ion mobility separator whilst the amplitude of the travelling DC voltage wave remains substantially constant.

The DC axial voltage gradient, the amplitude of the travelling wave and the velocity of the travelling DC voltage wave may also change with time. Hence, ions of differing mobility may first be separated spatially along the length of the ion guide and may then be moved along the ion mobility separator 1 to one end or the other. Ions may therefore be caused to exit the ion mobility separator 1 in increasing or decreasing order of their mobility.

Ions that have been separated according to their ion mobility may be caused to move to the exit of the ion mobility separator 1 by either reducing the DC potential gradient or by increasing the amplitude of the travelling DC voltage wave. These ions may also be moved to the exit of the ion mobility separator 1 by reducing the velocity of the travelling DC voltage wave or by reducing the gas pressure. Ions may also be caused to move by changing a combination of these controls. According to an embodiment ions may be caused to leave the ion mobility separator 1 in order of their ion mobility, starting with ions of highest mobility.

According to another embodiment the separated ions may be caused to move to the entrance of the ion mobility separator either by increasing the DC potential gradient and/or by reducing the amplitude of the travelling DC voltage wave and/or by increasing the velocity of the DC voltage wave and/or by increasing the gas pressure. According to this embodiment ions may be caused to be emitted from the ion mobility separator 1 via what was initially the entrance of the ion mobility separator 1 in order of their mobility starting with ions having the lowest ion mobility.

According to an embodiment the pulse amplitude, wave velocity, pressure and axial gradient may be varied during operation so as to enhance the separation.

A reversed axial voltage gradient may be used to enhance separation by constantly returning ions which have not been carried along by the travelling DC voltage wave to the entrance of the separation region.

According to an embodiment ions may be initially collected in an ion tunnel ion trap consisting of a stack of 90 ring electrodes each 0.5 mm thick and spaced apart by 1.0 mm. The central aperture of each ring may be 5.0 mm diameter and the total length of the ion tunnel ion trap may be 134 mm. A 2.1 MHz RF voltage may be applied between neighbouring rings to radially confine the ion beam within the ion trap. Ions may be retained in the ion tunnel ion trap by raising the DC potential at each end of the ion trap by approximately 5V. The pressure in the ion tunnel ion trap may be about $10^{-3}$ mbar.

Ions may be continuously generated using an Electrospray ion source and may be continuously directed into the ion tunnel ion trap. The DC potential at the exit end of the ion trap may then be periodically reduced to allow ions to exit the ion trap. Ions may be repeatedly collected and stored for, for example, 11 ms and then released over a period of, for example, 26 ns. Ions leaving the ion trap may then be accelerated through a 3 V potential difference and may optionally pass through a quadrupole rod set ion guide. The quadrupole rod set ion guide may in one mode of operation be operated with only RF voltage applied to the rods so that it acts as an ion guide and not as a mass filter. The ions exiting the quadrupole rod set ion guide may then enter an ion mobility separator 1 according to the preferred embodiment.

The ion mobility separator 1 may consist of a similar ion tunnel arrangement to that used for initially collecting and storing ions emitted from the ion source. The ion mobility separator 1 may consist of a stack of, for example, 122 ring electrodes, each 0.5 mm thick and spaced apart by 1.0 mm. The central aperture within each ring may be 5.0 mm diameter and the total length of ring stack may be 182 mm. A 2.4 MHz RF voltage may be applied between neighbouring rings to radially confine ions within the ion mobility separator 1. The pressure in the ion mobility separator 1 may be approximately $2 \times 10^{-2}$ mbar. A travelling DC voltage wave may be applied to the ion mobility separator 1 and may consist of a regular periodic pulse of constant amplitude and velocity.

The travelling DC voltage wave may be generated by applying a DC voltage to a single ring electrode and every subsequent ring displaced by nine rings along the ring stack. Hence, one wavelength $\lambda$ of the DC voltage waveform may consist of one electrode with a raised DC potential followed by eight electrodes held at a lower (reference) potential. Thus the wavelength $\lambda$ may be equivalent to the length of 9 electrodes or 13.5 mm and the total ion mobility separator may be equivalent to approximately 13.5 $\lambda$. The travelling DC voltage wave may be generated by applying approximately 0.65V to each ring electrode for 5 ns before moving the applied voltage to the next (adjacent) ring electrode. Thus the wave period or cycle time t according to this particular embodiment is 45 ns. This may be repeated uniformly along the length of the ion mobility separator 1. Thus the DC voltage wave velocity may be substantially equal to 300 mls according to one embodiment.

At the exit of the ion mobility separator 1 the ions may pass through a further quadrupole rod set.

This further quadrupole rod set may be operated in an RF and DC mode (i.e. mass filtering mode) and may be arranged to transmit only ions having a particular mass to charge ratio.

If a mixture of Gramicidin-S (mol wt 1142 daltons) and Leucine Enkephalin (mol wt 555 daltons) is continuously introduced into an Electrospray ion source then singly charged protonated ions of Leucine Enkephalin (m/z 556) and doubly charged protonated ions of Gramicidin-S (m/z 572) will be collected and stored in the upstream ion trap 4. These ions may then be periodically released and their transit times through the ion mobility separator 1 measured. The transit time of Gramicidin-S ions through the ion mobility separator 1 may, for example, be approximately 2.2 ms after release from the upstream ion trap 4 whereas the transit time of Leucine Enkephalin ions may, for example, be approximately 3.1 ms after release from the upstream ion trap 4. Accordingly, the transit time of Gramicidin-S through the ion mobility separator 1 may be about 940 ns less than that for Leucine Enkephalin ions. This is in spite of the fact that the mass to charge ratio of Gramicidin-S (572) is slightly greater than that for Leucine Enkephalin (556) and also that the Gramicidin-S molecule (mol wt 1142 daltons) is larger than the Leucine Enkephalin molecule (mol wt 555 daltons). However, the shorter transit time for Gramicidin-S may nonetheless be expected since Gramicidin-S ions are doubly charged and experience twice the force due to the electric field of the travelling wave than that experienced by singly charged Leucine Enkephalin ions.

Although doubly charged Gramicidin-S ions experience twice the force they will not experience twice the viscous drag since the cross-sectional area of Gramicidin-S ions is not twice that of Leucine Enkephalin ions. It may be estimated that their relative cross sectional areas are in the ratio of approximately $(1144/556)^{2/3}$ i.e. approximately 1.6. Hence, Gramicidin-S ions are more mobile than Leucine Enkephalin ions in the presence of the same electric field and same high gas pressure. Therefore, Gramicidin-S ions are more strongly affected by the travelling DC voltage waveform than Leucine Enkephalin ions. As a result, the transit time for Gramicidin-S ions through the ion mobility separator 1 is less than that for Leucine Enkephalin ions.

Figure 16:
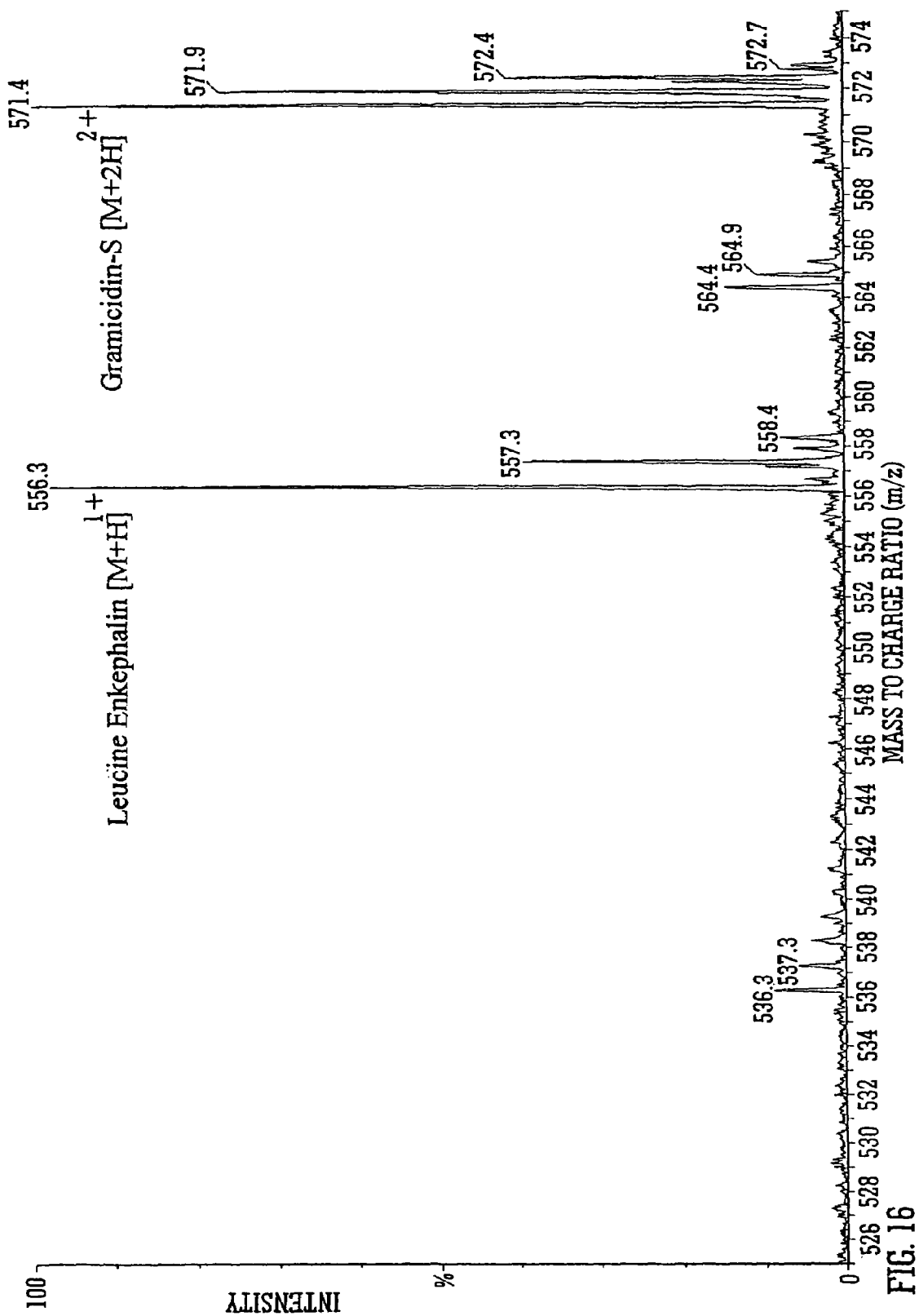
FIG. 16 shows a conventional mass spectrum of a mixture of singly charged Leucine Enkephalin ions and doubly charged Gramicidin-S ions.

FIG. 16 shows a conventional mass spectrum of singly and doubly charged ions from a mixture of 0.1 ng/$\mu$l Leucine Enkephalin and 0.1 ng/$\mu$l of Gramicidin-S.

Figure 17:
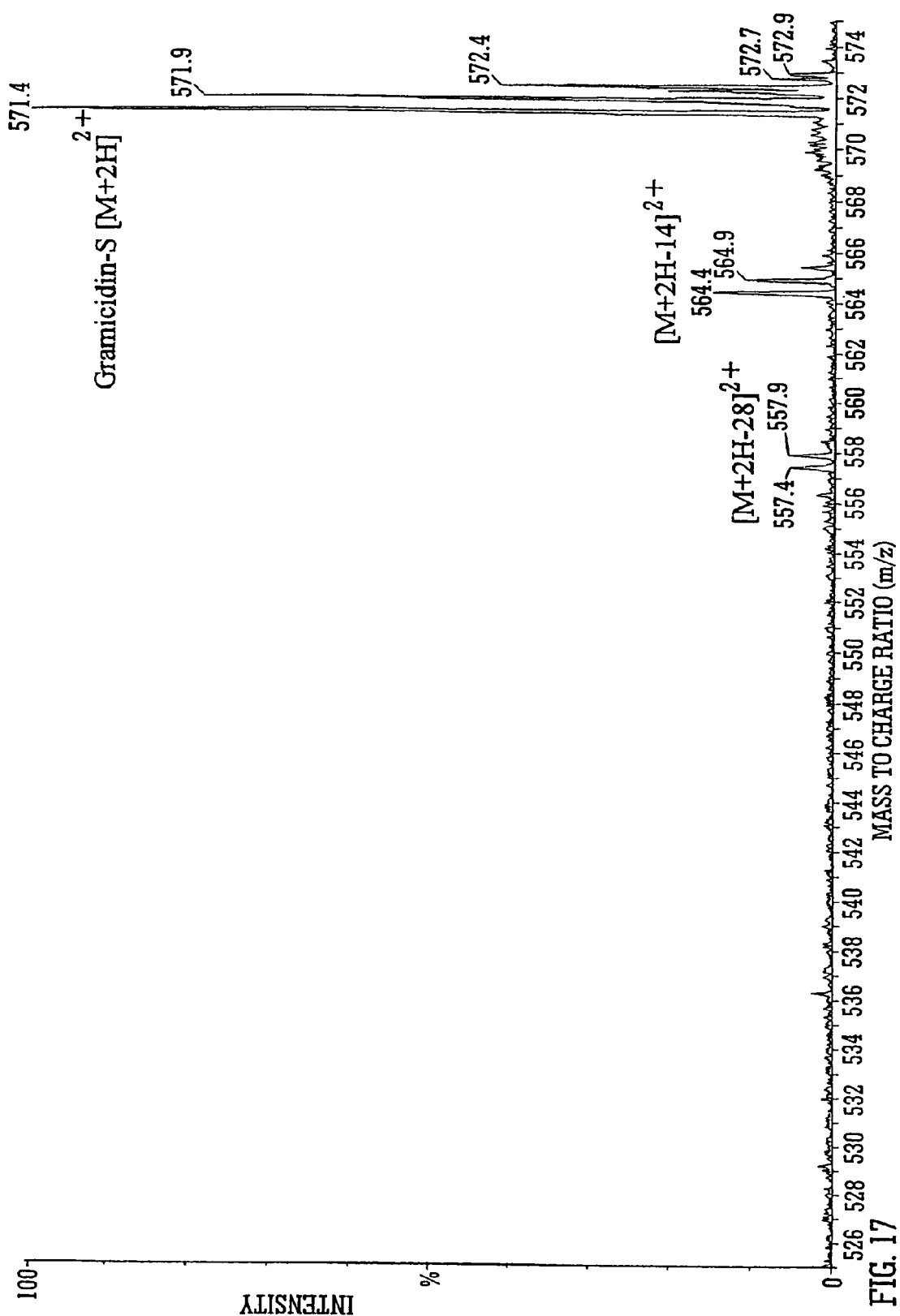
FIG. 17 shows a mass spectrum obtained according to a preferred embodiment of the present invention wherein the mass spectral data which was wholly used in the example shown in FIG. 16 has been processed so that singly charged Leucine Enkephalin ions are substantially absent from the resulting mass spectrum.

FIG. 17 shows a mass spectrum obtained according to the preferred embodiment wherein the mass spectral data used to produce the mass spectrum shown in FIG. 16 was processed according to the preferred embodiment so that ions having a flight time less than a minimum cut-off value (which is varied as a function of drift time through the ion mobility separator 1) were rejected or otherwise attenuated with the effect that singly charged ions from Leucine Enkephalin are substantially absent from the resulting mass spectrum. It will be appreciated from comparing FIGS. 16 and 17 that according to the preferred embodiment the signal to noise ratio has been significantly improved by a factor of approximately x100. If singly charged ions are viewed as being noise then embodiments of the present invention are contemplated wherein the signal to noise of mass peaks due to a doubly or multiply charged analyte ions is improved by at least a factor of x2, x3, x4, x5, x10, x20, x30, x40, x50, x60, x70, x80, x90, x100, x110, x120, x130, x140, x150, x160, x170, x180, x190, or x200.

According to an embodiment 100 pulses of ions are released into the ion mobility separator 1 at intervals of 10 ms over a 1s period of time. Each pulse of ions then results in 200 sets of mass spectral data since the repetition rate between successive energisations of the pusher electrode 6 was 50 $\mu$s. Corresponding sets of mass spectral data resulting from each pulse of ions into the ion mobility separator 1 may then be summed to produce 200 composite sets of mass spectral data.

Figure 18:
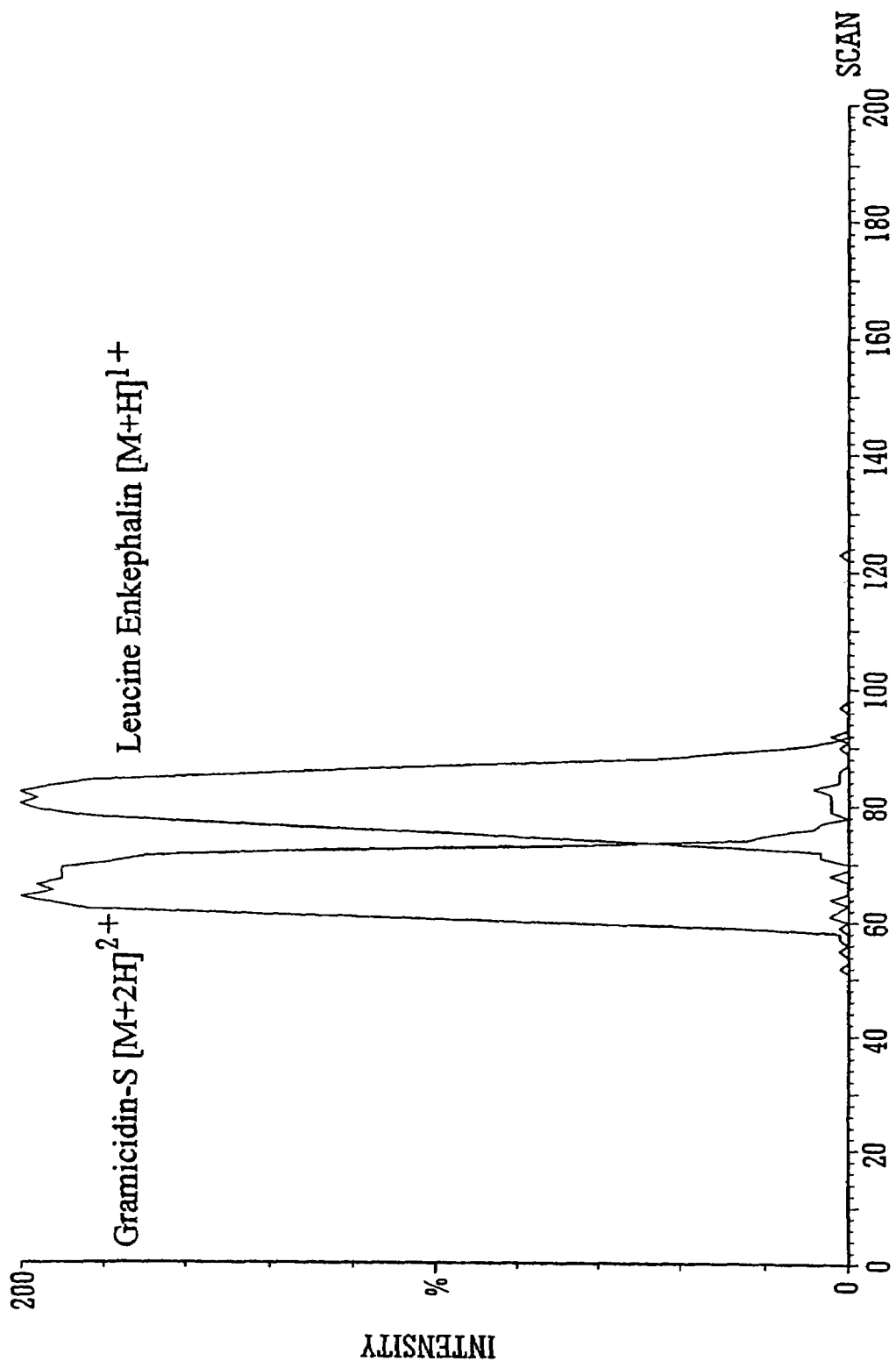
FIG. 18 shows an ion mobility spectrum for Leucine Enkephalin and Gramicidin-S ions.

FIG. 18 shows superimposed ion mobility spectra for Leucine Enkephalin and Gramicidin-S and shows that these two ions having similar mass to charge ratios can be resolved using the ion mobility separator 1.

The mass spectra and ion mobility spectra shown in FIGS. 16–18 were obtained using an ion mobility separator 1 having a plurality of ring electrodes and a constant axial DC voltage gradient as described previously.

According to a particularly preferred embodiment a Q-T of Ultima (RTM) API hybrid quadrupole orthogonal Time of Flight mass spectrometer (Micromass, UK) was modified to implement the preferred embodiment. A schematic of the mass spectrometer is shown in FIG. 19 with the modifications over the standard instrument being the replacement of an RF-only ion guide in the first transfer region 20 with an ion trap 4, ion gate 7 and ion mobility separator 1 and modification of the RF-only ion guide in the second transfer region 21 to allow generation of an axial voltage gradient e.g. by providing a stacked ring ion guide.

Figure 19:
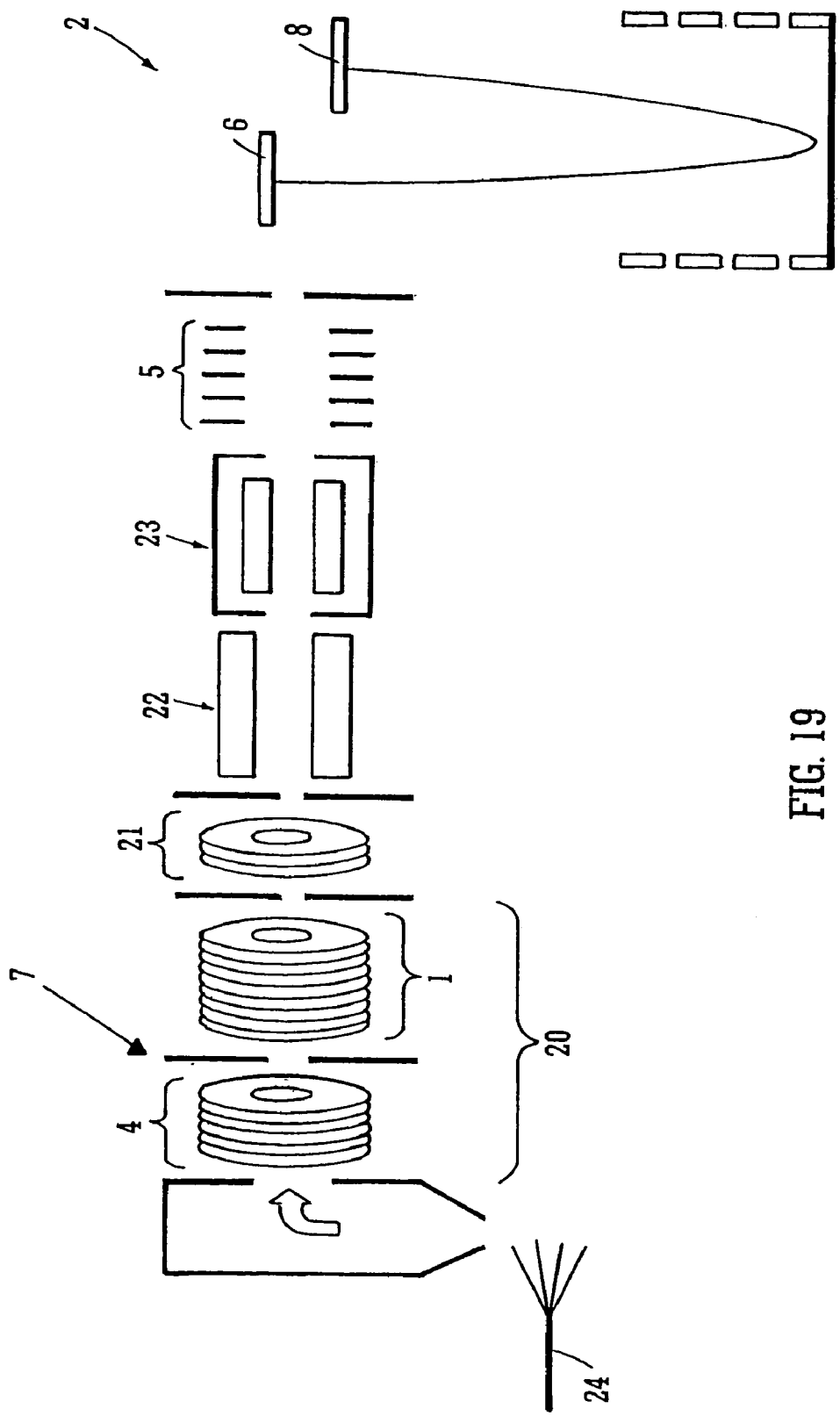
FIG. 19 shows a schematic diagram of a mass spectrometer according to a preferred embodiment.
Figure 20:
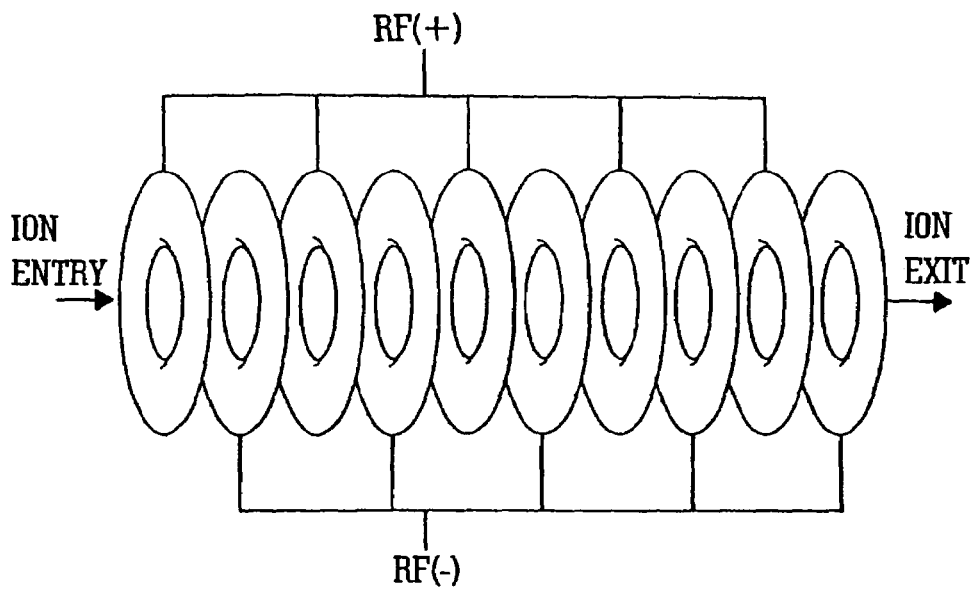
FIG. 20 illustrates a stacked ring ion mobility separator.

The ion trap 4, ion mobility separator 1 and ion guide used in the mass spectrometer shown in FIG. 19 preferably have a stacked ring electrode geometry as shown in FIG. 20 wherein adjacent electrodes are supplied with AC or RF voltages having an 180° phase difference. The ring electrodes are preferably 0.5 mm thick and are preferably spaced 1.5 mm centre-to-centre so that they have a nominal spacing of 1 mm and have a 5.0 mm diameter ion transmission aperture.

Figure 21:
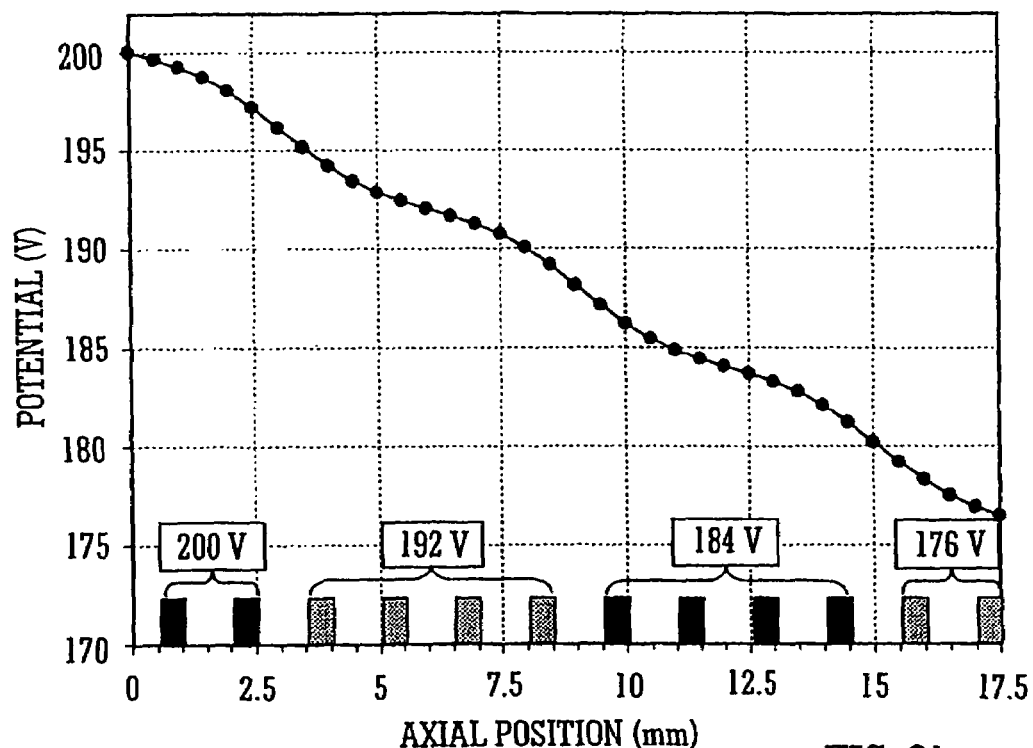
FIG. 21 illustrates the axial potential along a portion of a preferred ion mobility separator showing the slight non-uniformity in gradient due to the rings being grouped into groups of four electrodes wherein all the electrodes in a group are maintained at substantially the same DC potential.

The ion trap 4 may comprise an RF-only ion storage region which is preferably 75 mm long. The ion mobility separator 1 according to an embodiment is 152 mm long and has the same applied AC or RF voltages as the ion trap 4 but additionally is preferably segmented axially to facilitate generation of an axial electric field. The electrodes of the ion mobility separator 1 may be grouped into groups of four electrodes per segment with a common applied DC voltage to a segment. The groups of four electrodes are preferably interconnected by a resistor chain and the applied AC or RF voltages may be capacitively coupled to each same-phase electrode. Through application of different voltages at each end of the resistor chain an axial DC electric field can be produced. The generated field may not be axially uniform and may, for example, have a slightly stepped profile similar to that shown in FIG. 21. Between the ion trap 4 and the ion mobility separator 1 is a gate electrode 7 to allow pulsed delivery of ions for mobility separation. The gate electrode 7 preferably has a 2 mm aperture and no AC or RF voltage is preferably applied to the gate electrode 7. The gate voltage may be kept +10 V with respect to the voltage applied to the ion trap 4 in order to facilitate trapping of the negatively charged ions. The voltage may then be dropped to that of the ion trap 4 (or lower) for a short period (e.g. approximately 200 $\mu$s) to release ions into the ion mobility separator 1. The gate pulses may be generated using a LeCroy LW120 Arbitrary Wave Form Generator. The ion trap 4 and ion mobility separator 1 may be operated, for example, at a pressure of approximately 2.5 mbar. The applied RF voltage may have a frequency of 0.8 MHz and the peak to peak voltage may be set dependent on the masses of interest. The ion mobility separator 1 may be operated with a potential difference of 200 V giving rise to an average field of 13.2 V/cm.

The stacked ring ion guide 21 provided downstream of the ion mobility separator 1 according to an embodiment is 30.5 mm long and may be segmented axially to allow application of a DC axial field to reduce transit time of the ion packets produced by mobility separation. The stacked ring ion guide 21 may be maintained at a pressure of approximately $10^{-3}$ mbar. The ion guide 21 may be supplied with an RF voltage having a frequency of 1.9 MHz with a peak to peak voltage set depending on the mass range of interest. The potential difference across the ion guide 21 may, for example, be 2 V giving rise to an average axial field of 0.66 V/cm. A quadrupole mass filter 22 and a collision cell 23 may be provided downstream of the ion mobility separator 1 and the ion guide 21 as shown in FIG. 19 for performing MS/MS experiments.

Ions preferably continually flow into the ion trap 4 from an ion source, preferably on Electrospray ion source 24, and are preferably prevented from exiting the ion trap 4 by the application of a DC voltage to the ion gate 7. The gate voltage may then be pulsed to release ions into the ion mobility separator 1 where the ions separate according to their ion mobility. Having exited the ion mobility separator 1 the ions then pass through a transfer lens 5 before passing to the Time of Flight analyser 2 for mass analysis.

To determine the arrival time of mobility separated ion packets at the Time of Flight analyser 2, a modified Mass-Lynx (RTM) control and data acquisition system may be used. Time of flight data acquisition may be initiated by the voltage pulse applied to the ion gate 7 for releasing ions to the ion mobility separator 1. The subsequent two hundred or so orthogonal acceleration pulses applied to (or pushes of) the injection electrode 6 of the Time of Flight mass analyser 2 may then be recorded as individual mass spectra. The individual mass spectra from all the same nth pushout events may then be combined to form a number of composite mass spectra. If there are 200 pushout events per pulse of ions into the ion mobility separator 1 then 200 composite mass spectra will be generated.

The duration of individual mobility acquisitions depends upon the mass range of interest to be acquired and consequently on the pusher pulse repeat time. For example if a mass range of 1250 Da is required, then this would correspond to a 50 $\mu$s pusher repeat time and the total mobility experiment would then be recorded over a 10 ms (200×50 $\mu$s) time period The use of a fixed 200 pushes per mobility spectrum encompasses all expected ion drift times through the ion mobility separator 1. The mobility spectra may be summed for five seconds and then repeated for a further five seconds and so on until the acquisition is halted.

Embodiments are contemplated wherein the AC or RF voltage supplied to electrode(s) of the ion mobility separator 1 and/or ion trap 4 may be non-sinusoidal and may, for example, take the form of a square wave.

The embodiments described above have been described predominantly in relation to processing (or selectively recording) mass spectral data and effectively filtering out ions having a flight time (or mass to charge ratio) which falls outside of a desired range as a function of drift time. However, embodiments are also contemplated wherein the data may be in the form of ion mobility data which is then processed (or selectively recorded) to effectively-filter out ions having drifts time (or ion mobilities) outside of a desired range.

Although the present invention has been described with reference to preferred embodiments, it will be understood by those skilled in the art that many changes in form and detail may be made without departing from the scope of the invention as set forth in the accompanying claims.

What is claimed is:

1. A mass spectrometer comprising:
   an ion mobility separator for separating ions according to their ion mobility so that ions emerge from said ion mobility separator over different time intervals;
   a Time of Flight mass analyser comprising a flight region, said Time of Flight mass analyser arranged to mass analyse at least some of the ions of a first group of ions which emerge from said ion mobility separator during a first time interval; and
   processing means arranged to:
   (i) produce a first mass spectral set of data including data corresponding to the time of flight of at least some of the ions of said first group of ions through said flight region; and
   (ii) process said first mass spectral set of data to form a first processed mass spectral set of data wherein the intensity or significance of ions having a first undesired charge state is reduced relative to ions having a second different desired charge state.

2. A mass spectrometer as claimed in claim 1, wherein ions are pulsed at least x times into said ion mobility separator and wherein said first mass spectral set of data is a composite set of mass spectral data obtained by summing at least x sets of mass spectral data, wherein said x sets of mass spectral data relate to separate pulses of ions.

3. A mass spectrometer as claimed in claim 1, wherein at least some of the ions of at least n further groups of ions which emerge from said ion mobility separator during at least n further time intervals are mass analysed in use with said Time of Flight mass analyser.

4. A mass spectrometer as claimed in claim 3, wherein said processing means produces at least n further mass spectral sets of data each including data corresponding to the time of flight of at least some of the ions of said at least n further groups of ions through said flight region.

5. A mass spectrometer as claimed in claim 4, wherein ions are pulsed at least x times into said ion mobility separator and wherein said n further mass spectral sets of data are composite sets of mass spectral data wherein each composite set of mass spectral data is obtained by summing at least x sets of mass spectral data, wherein said x sets of mass spectral data relate to separate pulses of ions.

6. A mass spectrometer as claimed in claim 4, wherein said processing mean processes said at least n further mass spectral sets of data to form at least n further processed mass spectral sets of data wherein the intensity or significance of ions having said first undesired charge state is reduced relative to ions having said second desired charge state.

7. A mass spectrometer as claimed in claim 1, wherein said processing means processes said first and/or n further mass spectral sets of data by attenuating the intensity or significance of ions having a flight time less than a minimum flight time.

8. A mass spectrometer as claimed in claim 1, wherein said processing means processes said first and/or n further mass spectral sets of data by attenuating the intensity or significance of ions having a flight time less than a minimum flight time and greater than a maximum flight time.

9. A mass spectrometer as claimed in claim 1, wherein said processing means processes said first and/or n further mass spectral sets of data by attenuating the intensity or significance of ions having a flight time greater than a maximum flight time.

10. A mass spectrometer as claimed in claim 7, wherein n is selected from the group consisting of: (i) 1–10; (ii) 10–20; (iii) 20–30; (iv) 30–40; (v) 40–50; (vi) 50–60; (vii) 60–70;

(viii) 70–80; (ix) 80–90; (x) 90–100; (xi) 100–110; (xii) 110–120; (xiii) 120–130; (xiv) 130–140; (xv) 140–150; (xvi) 150–160; (xvii) 160–170; (xviii) 170–180; (xix) 180–190; (xx) 190–200; (xxi) 200–250; (xxii) 250–300; (xxiii) 350–400; (xxiv) 400–450; (xxv) 450–500; and (xxvi) >500.

11. A mass spectrometer as claimed in claim 7, wherein said minimum flight time and/or said maximum flight time is progressively increased or decreased when processing mass spectral sets of data which were obtained in subsequent time intervals.

12. A mass spectrometer as claimed in claim 11, wherein said minimum flight time and/or maximum flight time is progressively increased or decreased in: (i) a substantially continuous manner; (ii) a substantially stepped manner; (iii) a substantially linear manner; (iv) a substantially non-linear manner; or (v) a substantially exponential manner.

13. A mass spectrometer as claimed in claim 1, wherein said processing mean forms a mass spectrum using said first processed mass spectral set of data.

14. A mass spectrometer as claimed in claim 13, wherein said processing means forms a mass spectrum using said at least n further processed mass spectral sets of data.

15. A mass spectrometer comprising:
an ion mobility separator for separating ions according to their ion mobility so that ions emerge from said ion mobility separator over different time intervals;
a Time of Flight mass analyser comprising a flight region, said Time of Flight mass analyser arranged to mass analyse at least some of the ions which emerge from said ion mobility separator; and
processing means arranged to:
(i) produce a first ion mobility set of data including data corresponding to the drift time of at least some ions through said ion mobility separator; and
(ii) process said first ion mobility set of data to form a first processed ion mobility set of data wherein the intensity or significance of ions having a first undesired charge state is reduced relative to ions having a second different desired charge state.

16. A mass spectrometer as claimed in claim 15, wherein said first ion mobility set of data is a composite set of ion mobility data obtained by summing a plurality of sets of ion mobility data.

17. A mass spectrometer as claimed in claim 15, wherein said processing means processes said first and/or a plurality of further ion mobility sets of data by attenuating the intensity or significance of ions having a drift time through said ion mobility separator greater than a maximum drift time.

18. A mass spectrometer as claimed in claim 15, wherein said processing means processes said first and/or a plurality of further ion mobility sets of data by attenuating the intensity or significance of ions having a drift time through said ion mobility separator less than a minimum drift time and greater than a maximum drift time.

19. A mass spectrometer as claimed in claim 15, wherein said processing means processes said first and/or a plurality of further ion mobility sets of data by attenuating the intensity or significance of ions having a drift time through said ion mobility separator less than a minimum drift time.

20. A mass spectrometer as claimed in claim 17, wherein said minimum drift time and/or said maximum drift time is progressively increased or decreased when processing consecutive, following or neighbouring sets of ion mobility data.

21. A mass spectrometer as claimed in claim 20, wherein said minimum drift time and/or maximum drift time is progressively increased or decreased in: (i) a substantially continuous manner; (ii) a substantially stepped manner; (iii) a substantially linear manner; (iv) a substantially non-linear manner; or (v) a substantially exponential manner.

22. A mass spectrometer as claimed in claim 15, wherein said processing means forms a mass spectrum using said first processed ion mobility set of data.

23. A mass spectrometer as claimed in claim 22, wherein said processing means forms a mass spectrum using a plurality of further processed ion mobility sets of data.

24. A mass spectrometer as claimed in claim 15, wherein said first charge state comprises singly charged ions.

25. A mass spectrometer as claimed in claim 15, wherein said second charge state comprises multiply charged ions.

26. A mass spectrometer as claimed in claim 15, wherein said second charge state is selected from the group consisting of: (i) doubly charged ions; (ii) triply charged ions; (iii) quadruply charged ions; (iv) ions having five or more charges; (v) doubly and triply charged ions; (vi) ions having three or more charges; and (vii) ions having four or more charges.

27. A mass spectrometer as claimed in claim 15, wherein said ion mobility separator comprises a plurality of electrodes, each electrode having an aperture through which ions are transmitted in use, wherein a DC voltage gradient is maintained across at least a portion of said ion mobility separator and at least some of said electrodes are connected to an AC or RF voltage supply.

28. A mass spectrometer as claimed in claim 27, wherein said ion mobility separator comprises:
an upstream section comprising a first plurality of electrodes having apertures arranged in a vacuum chamber; and
a downstream section comprising a second plurality of electrodes having apertures arranged in a further vacuum chamber, said vacuum chamber being separated by a differential pumping aperture.

29. A mass spectrometer as claimed in claim 28, wherein at least some of the electrodes in said upstream section are supplied, in use, with an AC or RF voltage having a frequency within the range 0.1–3.0 MHz.

30. A mass spectrometer as claimed in claim 28, wherein said upstream section is maintained, in use, at a pressure within the range 0.1–10 mbar.

31. A mass spectrometer as claimed in claim 28, wherein at least some of said electrodes in said downstream section are supplied, in use, with an AC or RF voltage having a frequency within the range 0.1–3.0 MHz.

32. A mass spectrometer as claimed in claim 28, wherein said downstream section is maintained, in use, at a pressure within the range $10^{-3}$–$10^{-2}$ mbar.

33. A mass spectrometer as claimed in claim 28, wherein a first DC voltage gradient is maintained, in use, across at least a portion of said upstream section and a second DC voltage gradient is maintained, in use, across at least a portion of said downstream section, said first DC voltage gradient being greater than said second DC voltage gradient.

34. A mass spectrometer as claimed in claim 27, wherein at least 60%, 65%, 70%, 75%, 80%, 85%, 90%, 95% of said electrodes have apertures which are of substantially the same size or area.

35. A mass spectrometer as claimed in claim 15, wherein said ion mobility separator comprises a segmented rod set and wherein a DC voltage gradient is maintained across at least a portion of said ion mobility separator.

36. A mass spectrometer as claimed in claim 15, wherein said ion mobility separator comprises a drift tube together with one or more electrodes for maintaining an axial DC voltage gradient along at least a portion of said drift tube.

37. A mass spectrometer as claimed in claim 15, wherein said ion mobility separator comprises a plurality of electrodes wherein in use one or more transient DC voltages or one or more transient DC voltage waveforms are progressively applied to said electrodes so that at least some ions having a first ion mobility are separated from other ions having a second different ion mobility.

38. A mass spectrometer as claimed in claim 37, wherein said one or more transient DC voltages or said one or more transient DC voltage waveforms are such that at least 10%, 20%, 30%, 40%, 50%, 60%, 70%, 80%, 90% or 95% of said ions having said first ion mobility are moved along said ion mobility separator with a higher velocity than said ions having said second ion mobility.

39. A mass spectrometer as claimed in claim 15, wherein said ion mobility separator comprises a plurality of electrodes wherein in use one or more transient DC voltages or one or more transient DC voltage waveforms are progressively applied to said electrodes so that ions are moved towards a region of the ion mobility separator wherein at least one electrode has a potential such that at least some ions having a first ion mobility will pass across said potential whereas at least some other ions having a second different ion mobility will not pass across said potential.

40. A mass spectrometer as claimed in claim 39, wherein said one or more transient DC voltages or said one or more transient DC voltage waveforms are such that at least 10%, 20%, 30%, 40%, 50%, 60%, 70%, 80%, 90% or 95% of said ions having said first ion mobility pass across said potential.

41. A mass spectrometer as claimed in claim 39, wherein said one or more transient DC voltages or said one or more transient DC voltage waveforms are such that at least 10%, 20%, 30%, 40%, 50%, 60%, 70%, 80%, 90% or 95% of said ions having said second ion mobility will not pass across said potential.

42. A mass spectrometer as claimed in claim 37, wherein said one or more transient DC voltages or said one or more transient DC voltage waveforms are such that at least 10%, 20%, 30%, 40%, 50%, 60%, 70%, 80%, 90% or 95% of said ions having said first ion mobility exit said ion mobility separator substantially before ions having said second ion mobility.

43. A mass spectrometer as claimed in claim 37, wherein a majority of said ions having said first ion mobility exit said ion mobility separator a time t before a majority of said ions having said second ion mobility exit said ion mobility separator, wherein t falls within a range selected from the group consisting of: (i)<1 $\mu$s; (ii) 1–10 $\mu$s; (iii) 10–50 $\mu$s; (iv) 50–100 $\mu$s; (v) 100–200 $\mu$s; (vi) 200–300 $\mu$s; (vii) 300–400 $\mu$s; (viii) 400–500 $\mu$s; (ix) 500–600 $\mu$s; (x) 600–700 $\mu$s; (xi) 700–800 $\mu$s; (xii) 800–900 $\mu$s; (xiii) 900–1000 $\mu$s; (xiv) 1.0–1.1 ms (xv) 1.1–1.2 ms; (xvi) 1.2–1.3 ms; (xvii) 1.3–1.4 ms; (xviii) 1.4–1.5 ms; (xix) 1.5–1.6 ms; (xx) 1.6–1.7 ms; (xxi) 1.7–1.8 ms; (xxii) 1.8–1.9 ms; (xxiii) 1.9–2.0 ms; (xxiv) 2.0–2.5 ms; (xxv) 2.5–3.0 ms; (xxvi) 3.0–3.5 ms; (xxvii) 3.5–4.0 ms; (xxviii) 4.0–4.5 ms; (xxix) 4.5–5.0 ms; (xxx) 5–10 ms; (xxxi) 10–15 ms; (xxxii) 15–20 ms; (xxxiii) 20–25 ms; and (xxxiv) 25–30 ms.

44. A mass spectrometer as claimed in claim 15, wherein said ion mobility separator comprises a plurality of electrodes wherein in use one or more transient DC voltages or one or more transient DC voltage waveforms are progressively applied to said electrodes so that:

(i) ions are moved towards a region of the ion mobility separator wherein at least one electrode has a first potential such that at least some ions having first and second different ion mobilities will pass across said first potential whereas other ions having a third different ion mobility will not pass across said first potential; and then (ii) ions having said first and second ion mobilities are moved towards a region of the ion mobility separator wherein at least one electrode has a second potential such that at least some ions having said first ion mobility will pass across said second potential whereas other ions having said second different ion mobility will not pass across said second potential.

45. A mass spectrometer as claimed in claim 37, wherein said one or more transient DC voltages create: (i) a potential hill or barrier; (ii) a potential well; (iii) a combination of a potential hill or barrier and a potential well; (iv) multiple potential hills or barriers; (v) multiple potential wells; or (vi) a combination of multiple potential hills or barriers and multiple potential wells.

46. A mass spectrometer as claimed in claim 37, wherein said one or more transient DC voltage waveforms comprise: (i) a repeating waveform; or (ii) a square wave.

47. A mass spectrometer as claimed in claim 37, wherein said one or more transient DC voltage waveforms create a plurality of potential peaks or wells separated by intermediate regions.

48. A mass spectrometer as claimed in claim 47, wherein the DC voltage gradient in said intermediate regions: (i) is non-zero; (ii) is positive; (iii) is negative; (iv) is linear; (v) is non-linear; or (vi) increases exponentially; or (vii) decreases exponentially.

49. A mass spectrometer as claimed in claim 47, wherein the amplitude of said potential peaks or wells: (i) remains substantially constant; (ii) becomes progressively larger or smaller; or (iii) increases or decreases either linearly or non-linearly.

50. A mass spectrometer as claimed in claim 37, wherein in use an axial DC voltage gradient is maintained along at least a portion of the length of said ion mobility separator and wherein said axial voltage gradient varies with time.

51. A mass spectrometer as claimed in claim 37, wherein said ion mobility separator comprises 3, 4, 5, 6, 7, 8, 9, 10, 11, 12, 13, 14, 15, 16, 17, 18, 19, 20, 21, 22, 23, 24, 25, 26, 27, 28, 29, 30 or >30 segments, wherein each segment comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or >30 electrodes and wherein the electrodes in a segment are maintained at substantially the same DC potential.

52. A mass spectrometer as claimed in claim 51, wherein a plurality of segments are maintained at substantially the same DC potential.

53. A mass spectrometer as claimed in claim 51, wherein each segment is maintained, in use, at substantially the same DC potential as the subsequent yth segment wherein y is 3, 4, 5, 6, 7, 8, 9, 10, 11, 12, 13, 14, 15, 16, 17, 18, 19, 20, 21, 22, 23, 24, 25, 26, 27, 28, 29, 30 or >30.

54. A mass spectrometer as claimed in claim 37, wherein ions are confined radially, in use, within said ion mobility separator by an AC or RF electric field.

55. A mass spectrometer as claimed in claim 37, wherein ions are radially confined, in use, within said ion mobility separator in a pseudo-potential well and are moved axially along said ion mobility separator by a real potential barrier or well.

56. A mass spectrometer as claimed in claim 37, wherein in use one or more AC or RF voltage waveforms are applied to at least some of said electrodes so that ions are urged along at least a portion of the length of said ion mobility separator.

57. A mass spectrometer as claimed in claim 15, wherein the minimum, average or maximum transit time of ions through said ion mobility separator is selected from the group consisting of: (i) less than or equal to 20 ms; (ii) less than or equal to 10 ms; (iii) less than or equal to 5 ms; (iv) less than or equal to 1 ms; and (v) less than or equal to 0.5 ms.

58. A mass spectrometer as claimed in claim 15, wherein said ion mobility separator is maintained in use at a pressure selected from the group consisting of: (i) greater than or equal to 0.0001 mbar; (ii) greater than or equal to 0.0005 mbar; (iii) greater than or equal to 0.001 mbar; (iv) greater than or equal to 0.005 mbar; (v) greater than or equal to 0.01 mbar; (vi) greater than or equal to 0.05 mbar; (vii) greater than or equal to 0.1 mbar; (viii) greater than or equal to 0.5 mbar; (ix) greater than or equal to 1 mbar; (x) greater than or equal to 5 mbar; and (xi) greater than or equal to 10 mbar.

59. A mass spectrometer as claimed in claim 15, wherein said ion mobility separator is maintained in use at a pressure selected from the group consisting of: (i) less than or equal to 10 mbar; (ii) less than or equal to 5 mbar; (iii) less than or equal to 1 mbar; (iv) less than or equal to 0.5 mbar; (v) less than or equal to 0.1 mbar; (vi) less than or equal to 0.05 mbar; (vii) less than or equal to 0.01 mbar; (viii) less than or equal to 0.005 mbar; (ix) less than or equal to 0.001 mbar; (x) less than or equal to 0.0005 mbar; and (xi) less than or equal to 0.0001 mbar.

60. A mass spectrometer as claimed in claim 15, wherein said ion mobility separator is maintained, in use, at a pressure selected from the group consisting of: (i) between 0.0001 and 10 mbar; (ii) between 0.0001 and 1 mbar; (iii) between 0.0001 and 0.1 mbar; (iv) between 0.0001 and 0.01 mbar; (v) between 0.0001 and 0.001 mbar; (vi) between 0.001 and 10 mbar; (vii) between 0.001 and 1 mbar; (viii) between 0.001 and 0.1 mbar; (ix) between 0.001 and 0.01 mbar; (x) between 0.01 and 10 mbar; (xi) between 0.01 and 1 mbar; (xii) between 0.01 and 0.1 mbar; (xiii) between 0.1 and 10 mbar; (xiv) between 0.1 and 1 mbar; and (xv) between 1 and 10 mbar.

61. A mass spectrometer as claimed in claim 15, wherein said ion mobility separator is maintained, in use, at a pressure such that a viscous drag is imposed upon ions passing through said ion mobility separator.

62. A mass spectrometer as claimed in claim 37, wherein in use said one or more transient DC voltages or said one or more transient DC voltage waveforms are initially provided at a first axial position and are then subsequently provided at second, then third different axial positions along said ion mobility separator.

63. A mass spectrometer as claimed in claim 37, wherein said one or more transient DC voltages or said one or more transient DC voltage waveforms move from one end of said ion mobility separator to another end of said ion mobility separator so that at least some ions are urged along said ion mobility separator.

64. A mass spectrometer as claimed in claim 37, wherein said one or more transient DC voltages or said one more transient DC voltage waveforms move along said ion mobility separator with a velocity selected from the group consisting of: (i) 10–250 m/s; (ii) 250–500 m/s; (iii) 500–750 m/s; (iv) 750–1000 m/s; (v) 1000–1250 m/s; (vi) 1250–1500 m/s; (vii) 1500–1750 m/s; (viii) 1750–2000 m/s; (ix) 2000–2250 m/s; (x) 2250–2500 m/s; (xi) 2500–2750 m/s; (xii) 2750–3000 m/s; and (xiii)>3000 m/s.

65. A mass spectrometer as claimed in claim 37, wherein two or more transient DC voltages or two or more transient DC voltage waveforms pass simultaneously along said ion mobility separator.

66. A mass spectrometer as claimed in claim 15, wherein in use a continuous beam of ions is received at an entrance to said ion mobility separator.

67. A mass spectrometer as claimed in claim 15, wherein in use packets of ions are received at an entrance to said ion mobility separator.

68. A mass spectrometer as claimed in claim 15, wherein said ion mobility separator consists of: (i) 10–20 electrodes; (ii) 20–30 electrodes; (iii) 30–40 electrodes; (iv) 40–50 electrodes; (v) 50–60 electrodes; (vi) 60–70 electrodes; (vii) 70–80 electrodes; (viii) 80–90 electrodes; (ix) 90–100 electrodes; (x) 100–110 electrodes; (xi) 110–120 electrodes; (xii) 120–130 electrodes; (xiii) 130–140 electrodes; (xiv) 140–150 electrodes; or (xv) more than 150 electrodes.

69. A mass spectrometer as claimed in claim 15, wherein at least 10%, 20%, 30%, 40%, 50%, 60%, 70%, 80%, 90%, or 95% of the electrodes forming said ion mobility separator are connected to both a DC and an AC or RF voltage supply.

70. A mass spectrometer as claimed in claim 15, wherein axially adjacent electrodes of said ion mobility separator are supplied with AC or RF voltages having a phase difference of 180°.

71. A mass spectrometer as claimed in claim 15, further comprising an ion source selected from the group consisting of: (i) Electrospray ("ESI") ion source; (ii) Atmospheric Pressure Chemical Ionisation ("APCI") ion source; (iii) Atmospheric Pressure Photo Ionisation ("APPI") ion source; (iv) Matrix Assisted Laser Desorption Ionisation ("MALDI") ion source; (v) Laser Desorption Ionisation ("LDI") ion source; (vi) Inductively Coupled Plasma ("ICP") ion source; (vii) Electron Impact ("EI") ion source; (viii) Chemical Ionisation ("CI") ion source; (ix) a Fast Atom Bombardment ("FAB") ion source; (x) a Liquid Secondary Ion Mass Spectrometry ("LSIMS") ion source; (xi) a Field Ionisation ("FI") ion source; and (xii) a Field Desorption ("FD") ion source.

72. A mass spectrometer as claimed in claim 15, further comprising a continuous ion source.

73. A mass spectrometer as claimed in claim 15, further comprising a pulsed ion source.

74. A mass spectrometer as claimed in claim 71, wherein said ion source is coupled to a Gas Chromatograph ("GC") or a Liquid Chromatograph ("LC").

75. A mass spectrometer as claimed in claim 15, wherein said Time of Flight mass analyser comprises an injection electrode for injecting at least some ions in a direction substantially orthogonal to or parallel with an axis along which ions initially enter said Time of Flight mass analyser.

76. A mass spectrometer as claimed in claim 75, further comprising an ion trap upstream of said Time of Flight mass analyser for storing and periodically releasing ions into said Time of Flight mass analyser.

77. A mass spectrometer as claimed in claim 15, further comprising an ion trap for storing ions and periodically releasing ions to said ion mobility separator.

78. A mass spectrometer as claimed in claim 15, further comprising a collision cell wherein in one mode of operation at least some ions entering said collision cell are caused to fragment.

79. A mass spectrometer as claimed in claim 15, further comprising a mass filter downstream of said ion mobility separator.

80. A mass spectrometer comprising:
an ion mobility separator for separating ions according to their ion mobility so that ions emerge from said ion mobility separator over different time intervals;
a Time of Flight mass analyser comprising a flight region, said Time of Flight mass analyser arranged to mass analyse at least some of the ions of a first group of ions which emerge from said ion mobility separator during a first time interval; and
processing means arranged to record the time of flight of some of the ions of said first group of ions through said flight region to form a first mass spectral set of data wherein the intensity or significance of ions having a flight time less than a minimum flight time is reduced.

81. A mass spectrometer comprising:
an ion mobility separator for separating ions according to their ion mobility so that ions emerge from said ion mobility separator over different time intervals;
a Time of Flight mass analyser comprising a flight region, said Time of Flight mass analyser arranged to mass analyse at least some of the ions of a first group of ions which emerge from said ion mobility separator during a first time interval; and
processing means arranged to record the time of flight of some of the ions of said first group of ions through said flight region to form a first mass spectral set of data wherein the intensity or significance of ions having a flight time less than a minimum flight time and greater than a maximum flight time is reduced.

82. A mass spectrometer comprising:
an ion mobility separator for separating ions according to their ion mobility so that ions emerge from said ion mobility separator over different time intervals;
a Time of Flight mass analyser comprising a flight region, said Time of Flight mass analyser arranged to mass analyse at least some of the ions of a first group of ions which emerge from said ion mobility separator during a first time interval; and
processing means arranged to record the time of flight of some of the ions of said first group of ions through said flight region to form a first mass spectral set of data wherein the intensity or significance of ions having a flight time greater than a maximum flight time is reduced.

83. A mass spectrometer comprising:
an ion mobility separator for separating ions according to their ion mobility so that ions emerge from said ion mobility separator over different time intervals;
a Time of Flight mass analyser comprising a flight region, said Time of Flight mass analyser arranged to mass analyse at least some of the ions which emerge from said ion mobility separator; and
processing means arranged to record the drift time of at least some of the ions which emerge from said ion mobility separator to form a first ion mobility set of data wherein the intensity or significance of ions having a drift time through said ion mobility separator greater than a maximum drift time is reduced.

84. A mass spectrometer comprising:
an ion mobility separator for separating ions according to their ion mobility so that ions emerge from said ion mobility separator over different time intervals;
a Time of Flight mass analyser comprising a flight region, said Time of Flight mass analyser arranged to mass analyse at least some of the ions which emerge from said ion mobility separator; and
processing means arranged to record the drift time of at least some of the ions which emerge from said ion mobility separator to form a first ion mobility set of data wherein the intensity or significance of ions having a drift time through said ion mobility separator less than a minimum drift time and greater than a maximum drift time is reduced.

85. A mass spectrometer comprising:
an ion mobility separator for separating ions according to their ion mobility so that ions emerge from said ion mobility separator over different time intervals;
a Time of Flight mass analyser comprising a flight region, said Time of Flight mass analyser arranged to mass analyse at least some of the ions which emerge from said ion mobility separator; and
processing means arranged to record the drift time of at least some of the ions which emerge from said ion mobility separator to form a first ion mobility set of data wherein the intensity or significance of ions having a drift time through said ion mobility separator less than a minimum drift time is reduced.

86. A method of mass spectrometry comprising:
separating ions according to their ion mobility in an ion mobility separator so that ions emerge from said ion mobility separator over different time intervals;
mass analysing at least some of the ions of a first group of ions which emerge from said ion mobility separator during a first time interval with a Time of Flight-mass analyser, said Time of Flight mass analyser comprising a flight region;
producing a first mass spectral set of data including data corresponding to the time of flight of at least some of the ions of said first group of ions through said flight region; and
processing said first mass spectral set of data to form a first processed mass spectral set of data wherein the intensity or significance of ions having a first undesired charge state is reduced relative to ions having a second different desired charge state.

87. A method as claimed in claim 86, wherein ions are pulsed at least x times into said ion mobility separator and wherein said first mass spectral set of data is a composite set of mass spectral data obtained by summing at least x sets of mass spectral data, wherein said x sets of mass spectral data relate to separate pulses of ions.

88. A method as claimed in claim 86, further comprising mass analysing at least some of the ions of at least n further groups of ions which emerge from said ion mobility separator during at least n further time intervals with said Time of Flight mass analyser.

89. A method as claimed in claim 88, further comprising producing at least n further mass spectral sets of data each including data corresponding to the time of flight of at least some of the ions of said at least n further groups of ions through said flight region.

90. A method as claimed in claim 89, wherein ions are pulsed at least x times into said ion mobility separator and wherein said n further mass spectral sets of data are composite sets of mass spectral data wherein each composite set of mass spectral data is obtained by summing at least x sets of mass spectral data, wherein said x sets of mass spectral data relate to separate pulses of ions.

91. A method as claimed in claim 89, further comprising processing said at least n further mass spectral sets of data to form at least n further processed mass spectral sets of data wherein the intensity or significance of ions having said first undesired charge state is reduced relative to ions having said second desired charge state.

92. A method as claimed in claim 86, wherein said step of processing said first and/or n further mass spectral sets of data comprises attenuating the intensity or significance of ions having a flight time less than a minimum flight time.

93. A method as claimed in claim 86, wherein said step of processing said first and/or n further mass spectral sets of data comprises attenuating the intensity or significance of ions having a flight time less than a minimum flight time and greater than a maximum flight time.

94. A method as claimed in claim 86, wherein said step of processing said first and/or n further mass spectral sets of data comprises attenuating the intensity or significance of ions having a flight time greater than a maximum flight time.

95. A method as claimed in claim 92, wherein n is selected from the group consisting of: (i) 1–10; (ii) 10–20; (iii) 20–30; (iv) 30–40; (v) 40–50; (vi) 50–60; (vii) 60–70; (viii) 70–80; (ix) 80–90; (x) 90–100; (xi) 100–110; (xii) 110–120; (xiii) 120–130; (xiv) 130–140; (xv) 140–150; (xvi) 150–160; (xvii) 160–170; (xviii) 170–180; (xix) 180–190; (xx) 190–200; (xxi) 200–250; (xxii) 250–300; (xxiii) 350–400; (xxiv) 400–450; (xxv) 450–500; and (xxvi)>500.

96. A method as claimed in claim 92, wherein said minimum flight time and/or said maximum flight time is progressively increased or decreased when processing mass spectral sets of data which were obtained in subsequent time intervals.

97. A method as claimed in claim 96, wherein said minimum flight time and/or said maximum flight is progressively increased or decreased in: (i) a substantially continuous manner; (ii) a substantially stepped manner; (iii) a substantially linear manner; (iv) a substantially non-linear manner; or (v) a substantially exponential manner.

98. A method as claimed in claim 86, further comprising forming a mass spectrum comprises forming a mass spectrum using said first processed mass spectral set of data.

99. A method as claimed in claim 98, further comprising forming a mass spectrum using said at least n further processed mass spectral sets of data.

100. A method as claimed in claim 86, wherein said first charge state comprises singly charged ions.

101. A method as claimed in claim 86, wherein said second charge state comprises multiply charged ions.

102. A method as claimed in claim 86, wherein said second charge state is selected from the group consisting of: (i) doubly charged ions; (ii) triply charged ions; (iii) quadruply charged ions; (iv) ions having five or more charges; (v) doubly and triply charged ions; (vi) ions having three or more charges; and (vii) ions having four or more charges.

103. A method of mass spectrometry comprising:
separating ions according to their ion mobility in an ion mobility separator so that ions emerge from said ion mobility separator over different time intervals;
passing at least some of the ions of a first group of ions which emerge from said ion mobility separator during a first time interval to a Time of Flight mass analyser, said Time of Flight mass analyser comprising a flight region; and
recording the time of flight of some of the ions of said first group of ions through said flight region to form a first mass spectral set of data wherein the intensity or significance of ions having a flight time less than a minimum flight time is reduced.

104. A method of mass spectrometry comprising:
separating ions according to their ion mobility in an ion mobility separator so that ions emerge from said ion mobility separator over different time intervals;
passing at least some of the ions of a first group of ions which emerge from said ion mobility separator during a first time interval to a Time of Flight mass analyser, said Time of Flight mass analyser comprising a flight region; and
recording the time of flight of some of the ions of said first group of ions through said flight region to form a first mass spectral set of data wherein the intensity or significance of ions having a flight time less than a minimum flight time and greater than a maximum flight time is reduced.

105. A method of mass spectrometry comprising:
separating ions according to their ion mobility in an ion mobility separator so that ions emerge from said ion mobility separator over different time intervals;
passing at least some of the ions of a first group of ions which emerge from said ion mobility separator during a first time interval to a Time of Flight mass analyser, said Time of Flight mass analyser comprising a flight region; and
recording the time of flight of some of the ions of said first group of ions through said flight region to form a first mass spectral set of data wherein the intensity or significance of ions having a flight time greater than a maximum flight time is reduced.

106. A method of mass spectrometry comprising:
separating ions according to their ion mobility in an ion mobility separator so that ions emerge from said ion mobility separator over different time intervals;
passing at least some of the ions which emerge from said ion mobility separator to a Time of Flight mass analyser, said Time of Flight mass analyser comprising a flight region; and
recording the ion mobility of the ions of at least some of said ions to form a first ion mobility set of data wherein the intensity or significance of ions having a drift time through said ion mobility separator greater than a maximum drift time is reduced.

107. A method of mass spectrometry comprising:
separating ions according to their ion mobility in an ion mobility separator so that ions emerge from said ion mobility separator over different time intervals;
passing at least some of the ions which emerge from said ion mobility separator to a Time of Flight mass analyser, said Time of Flight mass analyser comprising a flight region; and
recording the ion mobility of the ions of at least some of said ions to form a first ion mobility set of data wherein the intensity or significance of ions having a drift time through said ion mobility separator less than a minimum drift time and greater than a maximum drift time is reduced.

108. A method of mass spectrometry comprising:
separating ions according to their ion mobility in an ion mobility separator so that ions emerge from said ion mobility separator over different time intervals;

passing at least some of the ions which emerge from said ion mobility separator to a Time of Flight mass analyser, said Time of Flight mass analyser comprising a flight region; and recording the ion mobility of the ions of at least some of said ions to form a first ion mobility set of data wherein the intensity or significance of ions having a drift time through said ion mobility separator less than a minimum drift time is reduced.

* * * * *